(12) United States Patent
Slilaty

(10) Patent No.: US 10,272,065 B2
(45) Date of Patent: Apr. 30, 2019

(54) GEM-DIFLUORINATED C-GLYCOSIDE COMPOUNDS AS ANTI-CANCER AGENTS

(71) Applicant: ADVANOMICS CORPORATION, Montreal (CA)

(72) Inventor: Steve N. Slilaty, Laval (CA)

(73) Assignee: Benoit & Côté, Montréal (CA)

( * ) Notice: Subject to any disclaimer, the term of this patent is extended or adjusted under 35 U.S.C. 154(b) by 0 days.

(21) Appl. No.: 14/760,021

(22) PCT Filed: Jan. 13, 2014

(86) PCT No.: PCT/CA2014/000029
§ 371 (c)(1),
(2) Date: Jul. 9, 2015

(87) PCT Pub. No.: WO2014/107803
PCT Pub. Date: Jul. 17, 2014

(65) Prior Publication Data
US 2015/0353573 A1    Dec. 10, 2015

Related U.S. Application Data

(60) Provisional application No. 61/752,075, filed on Jan. 14, 2013.

(51) Int. Cl.
| | |
|---|---|
| *A61K 31/365* | (2006.01) |
| *C07D 519/00* | (2006.01) |
| *C07D 309/10* | (2006.01) |
| *C07D 493/04* | (2006.01) |
| *A61K 45/06* | (2006.01) |
| *A61K 31/351* | (2006.01) |

(52) U.S. Cl.
CPC .......... *A61K 31/365* (2013.01); *A61K 31/351* (2013.01); *A61K 45/06* (2013.01); *C07D 309/10* (2013.01); *C07D 493/04* (2013.01); *C07D 519/00* (2013.01)

(58) Field of Classification Search
CPC .. C07D 493/04; C07D 309/10; C07D 519/00; A61K 31/365; A61K 45/06
USPC ............................................ 514/23; 536/120
See application file for complete search history.

(56) References Cited

U.S. PATENT DOCUMENTS

2009/0318675 A1* 12/2009 Quirion ................... C07H 3/02
536/18.1

FOREIGN PATENT DOCUMENTS

| CA | 2650384 A1 | 11/2007 |
| CA | 2822097 A1 | 6/2012 |

OTHER PUBLICATIONS

International Search Report of PCT/CA2014/000029; Denis Bélanger, dated Apr. 16, 2014.
Merzouki et al. "Adva-27a, a novel podophyllotoxin derivative found to be effective against multidrug-resistant human cancer cells", Anticancer Res., vol. 32, No. 10, pp. 4423-4432, 2012.
Allevi et al.: "A simple synthesis of C-Glucosides related to the antitumor agent etoposide", Journal of Carbohydrate Chemistry, vol. 12, No. 2, 1993, pp. 209-222.
Supplementary European Search Report of 14738145.3; Munich; dated Apr. 4, 2017; Gavriliu, Daniela.

* cited by examiner

*Primary Examiner* — Eric Olson
*Assistant Examiner* — Michael C. Henry
(74) *Attorney, Agent, or Firm* — Benoit & Cote, Inc.; Mathieu Miron

(57) ABSTRACT

The present document describes a synthesis of a class of gem-difluorinated C-glycoside compounds derived from podophyllotoxin, which may be used, but not exclusively, in oncology for the treatment of cancer. More particularly, the podophyllotoxin gem-difluorinated C-glycoconjugated derivatives display improved conformational and chemical stability, and improved cytotoxicity exhibited against drug-resistant cancer cell lines.

2 Claims, 5 Drawing Sheets

Example 1  Example 2

Example 1  Example 2

GEM-DIFLUORINATED C-GLYCOSIDE COMPOUNDS AS ANTI-CANCER AGENTS

CROSS-REFERENCE TO RELATED APPLICATIONS

This application is a US National Phase application under 35 USC § 371 of PCT/CA2014/000029, filed Jan. 14, 2013, which claims priority from and the benefit of U.S. Patent Application No. 61/752,075, filed on Jan. 14, 2013, the specification of which are hereby incorporated by reference.

BACKGROUND (a) Field

The subject matter disclosed generally relates to novel chemical compounds and methods. More particularly, the invention provides novel derivatives of podophyllotoxin with a gem-difluoronated compound, having improved conformational and chemical stability, and having improved cytotoxicity, and methods of synthesizing and using such compounds. Preferred compounds are useful for the treatment of abnormal cell growth, such as cancers.

(b) Related Prior Art

Podophyllotoxin 1 is a lignan isolated from the roots of two plants *Podophyllum peltatum* (North America) and *Podophyllum emodi* (Asia). It has strong antimitotic activity by inhibiting polymerization of tubulin. Too toxic to be used in chemotherapy, it has given rise to many antitumoral compounds after structural modifications. Among them, glycosylated derivatives, compounds which are usually less toxic and more water-soluble, have emerged. For example, etoposide 2 is used in the treatment of small-cell lung cancer, bladder and testicular cancer, lymphomas, acute leukemias, and Kaposi sarcomas.

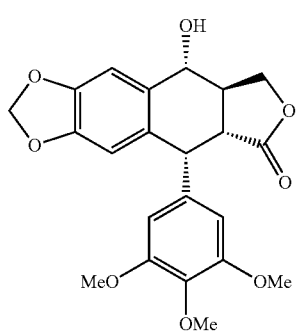

Podophyllotoxin 1

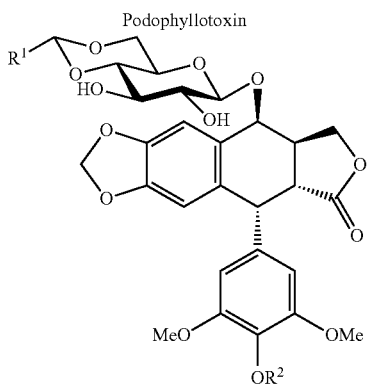

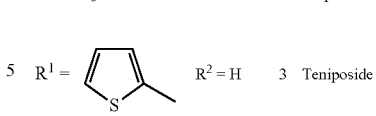  2 Etoposide

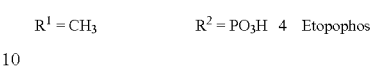  3 Teniposide $R^1 = CH_3$    $R^2 = PO_3H$    4 Etopophos

Nitrogen-containing derivatives of podophyllotoxin such as GL-331 5, NPF 6 or TOP-53 7 also show very interesting activities.

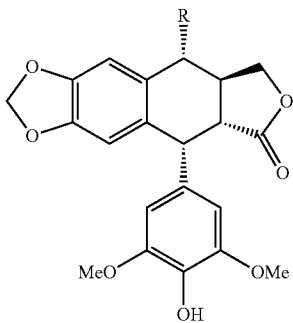

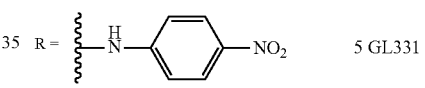  5 GL331

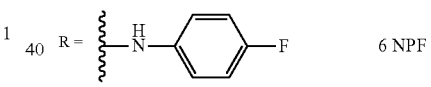  6 NPF

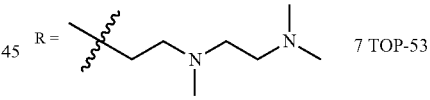  7 TOP-53

These molecules derived from the demethylepipodophyllotoxin structure, such as compound 2, 3 and 4, are inhibitors of topoisomerase II, an enzyme which catalyzes nicking and then reformation of the two DNA strands.

Nitrogen-containing compounds of podophyllotoxin, with an amine function substituted with a gem-difluorinated glycoside have been reported in U.S. Pat. No. 8,236,935. These compounds, 8 and 9, have significant cytotoxicity and the presence of a glycoside moiety improves the solubility of these compounds in aqueous medium and the gem-difluoromethylene group not only mimics the oxygen atom, but also prevents the hydrolysis of the glycoside moiety from the core structure, thus improving the pharmacological activity of these molecules. However, this class of molecules exists as an anomeric mixture with unstable conformations which may suffer from degradation driven by ring-opening process, thus resulting in loss of biological activities, and potentially poor pharmacokinetics properties.

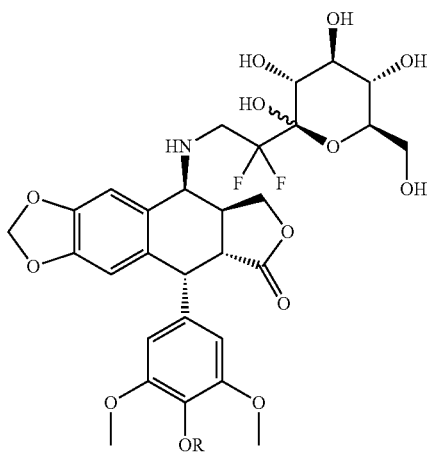

R = Me 8
R = H  9

Therefore, there is a need for derivatives of podophyllotoxin with a gem-difluoronated compound having improved conformational stability.

Furthermore, there is a need for derivatives of podophyllotoxin with a gem-difluoronated compound having improved chemical stability.

Furthermore, there is a need for derivatives of podophyllotoxin with a gem-difluoronated compound having improved cytotoxicity against cancer cells.

Also, there is a need for novel synthetic methods and processes to synthesize derivatives of podophyllotoxin with a gem-difluoronated compound.

SUMMARY

The present invention describes a novel class of derivatives of podophyllotoxin with a gem-difluoronated and a fixed glycoside ring. In addition to the improved conformational and chemical stabilities, the novel class of compounds of the present invention also unexpectedly exhibits significantly improved cytotoxicity against several cancer cell-lines, especially against those that are drug-resistant. The present invention also describes novel synthetic methods and processes to synthesize these novel compounds, which are not accessible previously via published procedures. Such compounds could be used as chemotherapy agents in the treatment of different types of cancer, either alone or associated with other treatments such as chemotherapies.

According to an embodiment, there is provided a compound of Formula I:

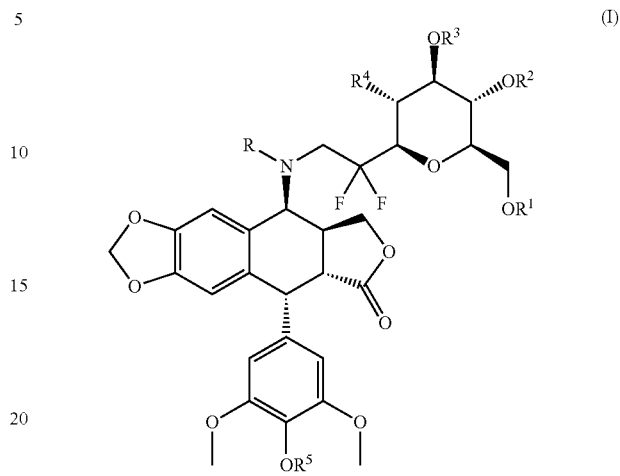

or a pharmaceutically acceptable salt, hydrate or solvate thereof, wherein: R may be a hydrogen atom or a group chosen from a linear or branched alkyl, benzyl, acetyl, or benzoyl group, $R^1$ and $R^2$, are identical or different, and are a hydrogen atom or a protective group for a hydroxyl group chosen from a linear or branched alkyl, benzyl, benzoyl, acetyl, or pivaloyl group, or an acetal group of the CR'R" type, where R' and R" are identical or different and are a hydrogen atom or a group chosen from a linear or branched alkyl, aryl, or alkyl-aryl group, $R^3$ may be a hydrogen atom or a group chosen from a linear or branched alkyl, benzyl, benzoyl, acetyl, or pivaloyl group, $R^4$ represents OR''', NGR'GR", $N_3$, or a phthalimide, where R''' may be a hydrogen atom or a protective group for a hydroxyl group chosen from a linear or branched alkyl, benzyl, benzoyl, acetyl, or pivaloyl group, and GR' and GR" are identical or different, and are a hydrogen atom or a group chosen from a linear or branched alkyl, benzyl, benzoyl, acetyl, al kyloxycarbonyl, allyloxycarbonyl, or benzyloxycarbonyl group, $R^5$ may be a hydrogen atom or a group chosen from a linear or branched alkyl, acetyl, benzyl, $PO_3H$, or $PO_3Na$ group.

According to another embodiment, there is provided a compound of Formula II:

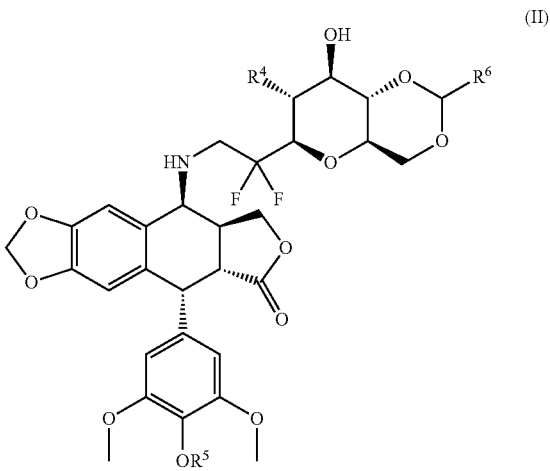

or a pharmaceutically acceptable salt, hydrate or solvate thereof, wherein:

$R^4$, $R^5$ are as defined above, $R^6$ may be a hydrogen atom or a group chosen from an alkyl, an aryl, an alkyl-aryl, a heteroaryl, or an alkyl-heteroaryl group.

According to another embodiment, there is provided a compound of Formula III:

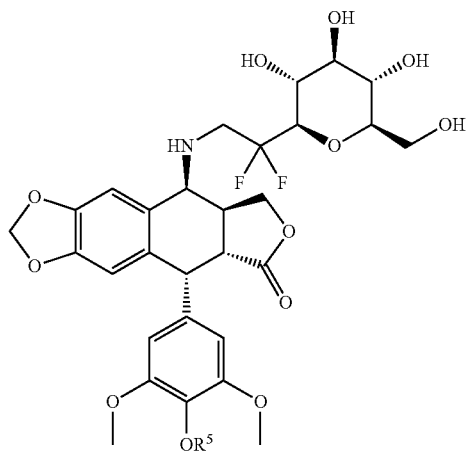

(III)

or a pharmaceutically acceptable salt, hydrate or solvate thereof, wherein:

$R^5$ may be a hydrogen atom, or a group chosen from an alkyl, —$PO_3H$ or —$PO_3Na$.

The compound is: (5R,5aR,8aS,9S)-9-((2,2-difluoro-2-((2R,3R,4S,5S,6R)-3,4,5-trihydroxy-6-(hydroxymethyl)tetrahydro-2H-pyran-2-yl)ethyl)amino)-5-(4-hydroxy-3,5-dimethoxyphenyl)-5,5a,8a,9-tetrahydrofuro[3',4':6,7]naphtho[2,3-d][1,3]dioxol-6(8H)-one.

The compound is: (5R,5aR,8aS,9S)-9-((2,2-difluoro-2-((2R,3R,4S,5S,6R)-3,4,5-trihydroxy-6-(hydroxymethyl)tetrahydro-2H-pyran-2-yl)ethyl)amino)-5-(3,4,5-trimethoxyphenyl)-5,5a,8a,9-tetrahydrofuro[3',4':6,7]naphtho[2,3-d][1,3]dioxol-6(8H)-one.

According to another embodiment, there is provided a method for preparing a compound of the present invention comprising a coupling step between a compound of Formula IV:

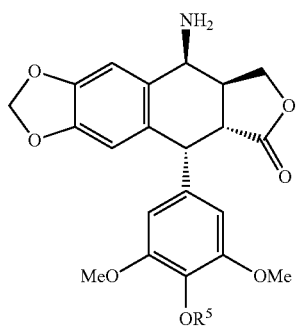

Formula IV wherein $R^5$ may be as defined in Formula I to III and a compound of Formula V:

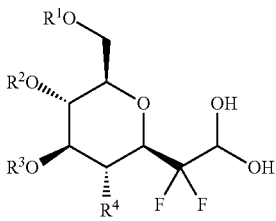

Formula V or a compound of Formula VI:

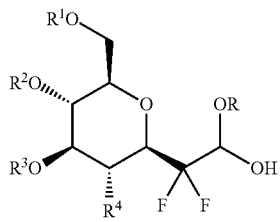

Formula VI wherein
$R^1$, $R^2$, $R^3$, $R^4$ are as defined in Formula I,
R may be a $C_1$-$C_{12}$ alkyl, and
wherein said compound of formula IV may be obtained by epimerization and then by substituting the alcohol function in position 4 of podophyllotoxin or demethylated podophyllotoxin by an azido group subsequently reduced into an amine group.

According to another embodiment, there is provided a compound of formula (VII) or (VIII):

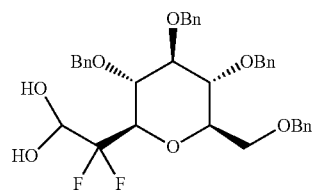

(VII)

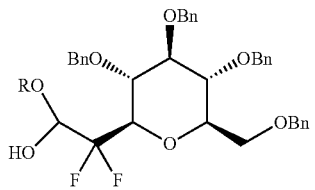

(VIII)

wherein R may be a group chosen from methyl, ethyl, butyl, or isopropyl group.

According to another embodiment, there is provided a use of at least one compound according to the present invention for preparing a medicament for the treatment of cancer.

According to another embodiment, there is provided a use of at least one compound according to the present invention for the treatment of cancer.

The use may be in combination with radiotherapy.

The use may be in combination with one or more other anti-cancer agents.

The cancer may be chosen from a bladder cancer, a brain cancer, a breast cancer, an uterus cancer, a chronic lymphoid leukemia, a colon cancer, an esophagus cancer, a liver cancer, a testicular cancer, a lymphoblastic leukemia, a follicular lymphomas, a melanomas, a malignant homeopathies, a myelomas, an ovarian cancer, a non-small-cell lung cancer, a prostate cancer, a small-cell lung cancer, an acute leukemia, a Kaposi sarcoma, and a lymphoid malignancy.

According to another embodiment, there is provided a method of treating a patient afflicted with cancer by administering to the patient a therapeutically effective amount of a compound of the present invention.

According to another embodiment, there is provided a method of treating a patient afflicted with cancer by administering to the patient a therapeutically effective amount of a compound of the present invention in combination with radiotherapy.

According to another embodiment, there is provided a method of treating a patient afflicted with cancer by administering to the patient a therapeutically effective amount of a compound of the present invention in combination with one or more other anti-cancer agents.

The cancer may be chosen from a cancer of bladder, a cancer of brain, a cancer of breast, a cancer of uterus, a chronic lymphoid leukemia, a colon cancer, an esophagus cancer, a liver cancer, a lymphoblastic leukemia, a follicular lymphomas, a melanomas, a malignant homeopathies, a myelomas, an ovarian cancer, a non-small-cell lung cancer, a prostate cancer, a small-cell lung cancer, and a lymphoid malignancy.

The following terms are defined below.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "Fluoroalkyl" means alkyl as defined above wherein one or more hydrogen atoms are replaced by fluoro atoms.

The term "Alkylene" by itself or as part of another substituent means a divalent radical derived from an alkyl, as exemplified, but not limited, by —CH$_2$CH$_2$CH$_2$CH$_2$—, —CH$_2$CH=CHCH$_2$—, —CH$_2$C≡CCH$_2$—, —CH$_2$CH$_2$CH(CH$_2$CH$_2$CH$_3$)CH$_2$—. Typically, an alkyl (or alkylene) group has from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

The term "Cycloalkyl" means mono- or bicyclic saturated carbocyclic rings, each of which having from 3 to 10 carbon atoms. A "fused analog" of cycloalkyl means a monocyclic rings fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, and the like.

The term "Alkoxy" means alkoxy groups of a straight or branched chain having the indicated number of carbon atoms. $C_{1-6}$alkoxy, for example, includes methoxy, ethoxy, propoxy, isopropoxy, and the like.

The term "Heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The term "Cycloalkoxy" means cycloalkyl as defined above bonded to an oxygen atom, such as cyclopropyloxy.

The term "Fluoroalkoxy" means alkoxy as defined above wherein one or more hydrogen atoms are replaced by fluoro atoms.

The term "Aryl" means mono- or bicyclic aromatic rings containing only carbon atoms. A "fused analog" of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, dihydrobenzopyranyl, 1,4-benzodioxanyl, and the like.

The term "Heteroaryl" means a mono- or bicyclic aromatic ring containing at least one heteroatom selected from N, O and S, with each ring containing 5 to 6 atoms. A "fused analog" of heteroaryl means a heteroaryl group fused to a monocyclic cycloalkyl or monocyclic heterocyclyl group in which the point of attachment is on the aromatic portion. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

The said alkyl groups, cycloalkyl, alkynyl, alkenyl, aryl groups and heteroaryl groups referred to in the definitions are unsubstituted or are substituted by at least one substituent selected from the group consisting of substituents.

The said substituents are selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent-x groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl(alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;

The term "Heterocyclyl" means mono- or bicyclic saturated rings containing at least one heteroatom selected from N, S and O, each of said ring having from 3 to 10 atoms in which the point of attachment may be carbon or nitrogen. A "fused analog" of heterocyclyl means a monocyclic heterocycle fused to an aryl or heteroaryl group in which the point of attachment is on the non-aromatic portion. Examples of "heterocyclyl" and fused analogs thereof include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

The term "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, trifluoromethyl, 2,2,2-trifluoroethyl, 4-chlorobutyl, 3-bromopropyl, and the like.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzyl ethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydramine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is alkaline, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
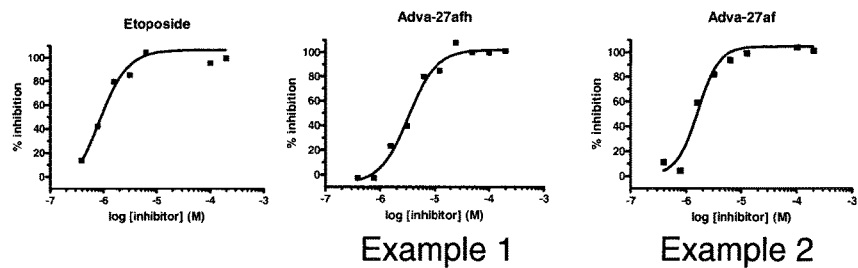
FIG. 1 illustrates the inhibition of human topoisomerase II DNA decatenation in the absence of BSA.

In embodiments there is disclosed compounds of Formula I, and tautomers and pharmaceutically acceptable salts and solvate thereof:

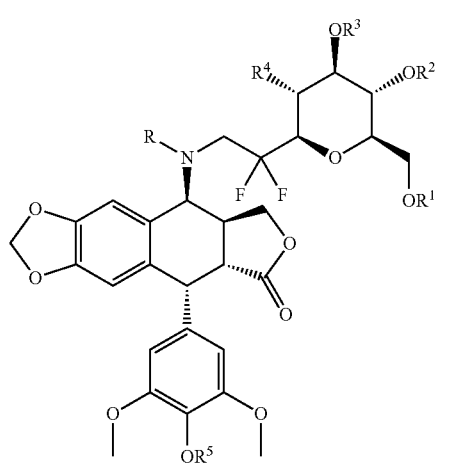

(I)

or a pharmaceutically acceptable salt, hydrate or solvate thereof, wherein:

R is a hydrogen atom or a group chosen from a linear or branched alkyl, benzyl, acetyl, or benzoyl group, $R^1$ and $R^2$, are identical or different, and are a hydrogen atom or a protective group for a hydroxyl group chosen from a linear or branched alkyl, benzyl, benzoyl, acetyl, or pivaloyl group, or an acetal group of the CR'R" type, where R' and R" are identical or different and are a hydrogen atom or a group chosen from a linear or branched alkyl, aryl, or alkyl-aryl group, $R^3$ is a hydrogen atom or a group chosen from a linear or branched alkyl, benzyl, benzoyl, acetyl, or pivaloyl group, $R^4$ represents OR''', NGR'GR", $N_3$, or a phthalimide, where R''' is a hydrogen atom or a protective group for a hydroxyl group chosen from a linear or branched alkyl, benzyl, benzoyl, acetyl, or pivaloyl group, and GR' and GR" are identical or different, and are a hydrogen atom or a group chosen from a linear or branched alkyl, benzyl, benzoyl, acetyl, alkyloxycarbonyl, allyloxycarbonyl, or benzyloxycarbonyl group, $R^5$ is a hydrogen atom or a group chosen from a linear or branched alkyl, acetyl, benzyl, $PO_3H$, or $PO_3Na$ group.

According to an embodiment, the invention also includes derivatives in the state of a base, of a mineral or organic acid addition salt or a hydrate or a pharmaceutically acceptable solvate of the compound of formula (I).

According to another embodiment, there is disclosed a compound of Formula II:

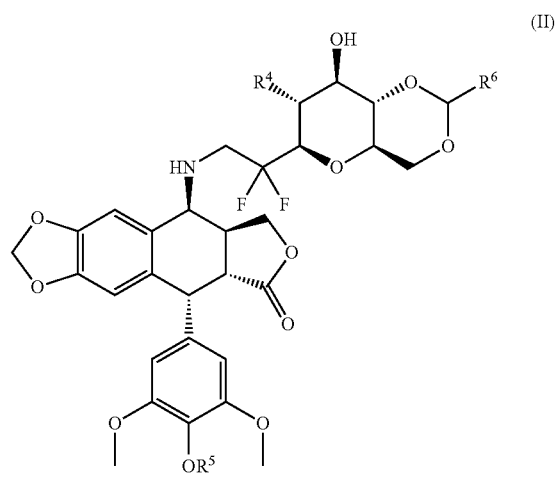

(II)

or a pharmaceutically acceptable salt, hydrate or solvate thereof, wherein:

$R^4$, $R^5$ are as defined above in Formula I, $R^6$ is a hydrogen atom or a group chosen from an alkyl, an aryl, an alkyl-aryl, a heteroaryl, or an alkyl-heteroaryl group.

According to an embodiment, the invention also includes derivatives in the state of a base, of a mineral or organic acid addition salt or a hydrate or a pharmaceutically acceptable solvate of the compound of formula (II).

According to another embodiment, there is disclosed a compound of Formula III:

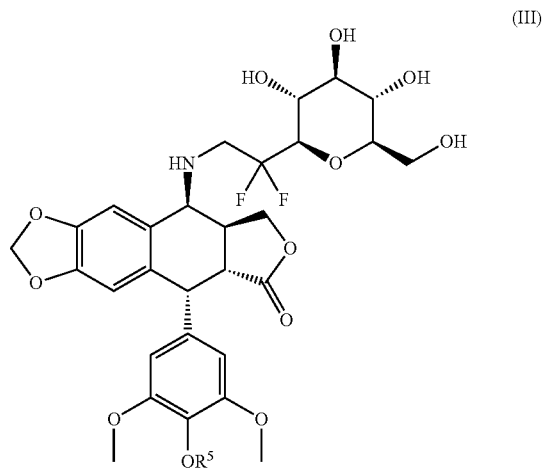

(III)

or a pharmaceutically acceptable salt, hydrate or solvate thereof, wherein:

R⁵ is a hydrogen atom, or a group chosen from an alkyl, —PO₃H or —PO₃Na.

According to another embodiment, there is disclosed a compound of formula (III) which is:

(5R,5aR,8aS,9S)-9-((2,2-difluoro-2-((2R,3R,4S,5S,6R)-3,4,5-trihydroxy-6-(hydroxymethyl)tetrahydro-2H-pyran-2-yl)ethyl)amino)-5-(4-hydroxy-3,5-dimethoxyphenyl)-5,5a,8a,9-tetrahydrofuro[3',4':6,7]naphtho[2,3-d][1,3]dioxol-6(8H)-one.

According to another embodiment, there is disclosed a compound of formula (III) which is:

(5R,5aR,8aS,9S)-9-((2,2-difluoro-2-((2R,3R,4S,5S,6R)-3,4,5-trihydroxy-6-(hydroxymethyl)tetrahydro-2H-pyran-2-yl)ethyl)amino)-5-(3,4,5-trimethoxyphenyl)-5,5a,8a,9-tetrahydrofuro[3',4':6,7]naphtho[2,3-d][1,3]dioxol-6(8H)-one.

In Formulae I to III, the alkyl group may be linear or branched alkyl groups having 1 to 10 carbon atoms. The alkyl group may be substituted with one or more halogen atom(s), alkyloxy, alkylthio, —OC(O)alkyl —OC(O)Oalkyl, —OC(O)aryl and O(O)Oaryl. The aryl group means mono- or bicyclic aromatic rings containing only carbon atoms. The heteroaryl means a mono- or bicyclic aromatic ring containing at least one heteroatom selected from N, O and S, with each ring containing 5 to 6 atoms.

The compounds of general Formulae I to III as defined above, i.e. including their derivatives in the state of a base, of a mineral or organic acid addition salt, of a hydrate or of a possibly pharmaceutically acceptable solvate may appear as different galenic forms adapted to their use, for example injectable solutions or suspensions.

Compounds of the Formula I may be separated into diastereoisomeric pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine or acid as a resolving agent or on a chiral HPLC column.

One or more than one of the protons in compounds of Formula I to III can be replaced with deuterium atom(s), thus providing deuterated analogs that may have improved pharmacological activities.

According to another embodiment, there is disclosed a method for the preparation of the compounds of the present invention. The method comprises a coupling step between a compound of Formula IV:

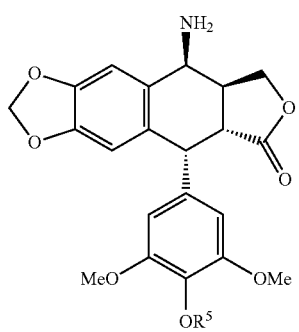

Formula IV wherein R⁵ is as defined in Formula I to III and a compound of Formula V:

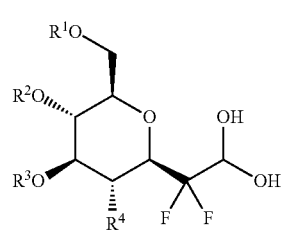

Formula V or a compound of Formula VI:

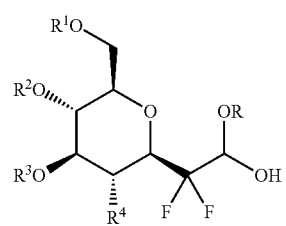

Formula VI wherein

R¹, R², R³, R⁴ are as defined in Formula I,

R is a C₁-C₁₂ alkyl, and the compound of formula IV is obtained by epimerization and then by substituting the alcohol function in position 4 of podophyllotoxin or demethylated podophyllotoxin by an azido group subsequently reduced into an amine group.

The compound of Formula V is obtained via the following scheme:

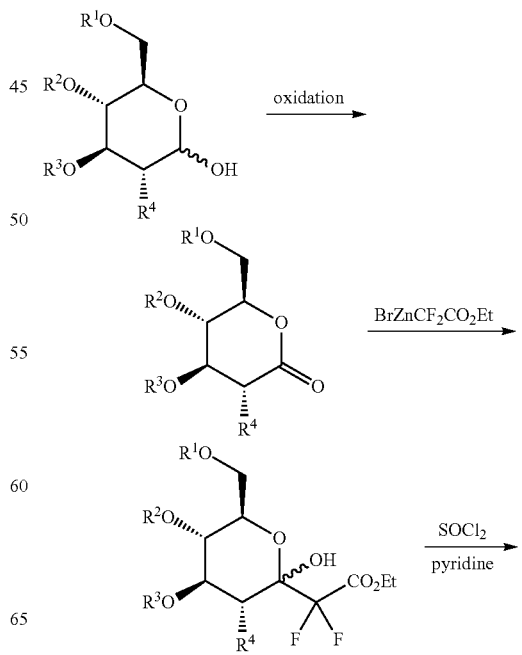

-continued

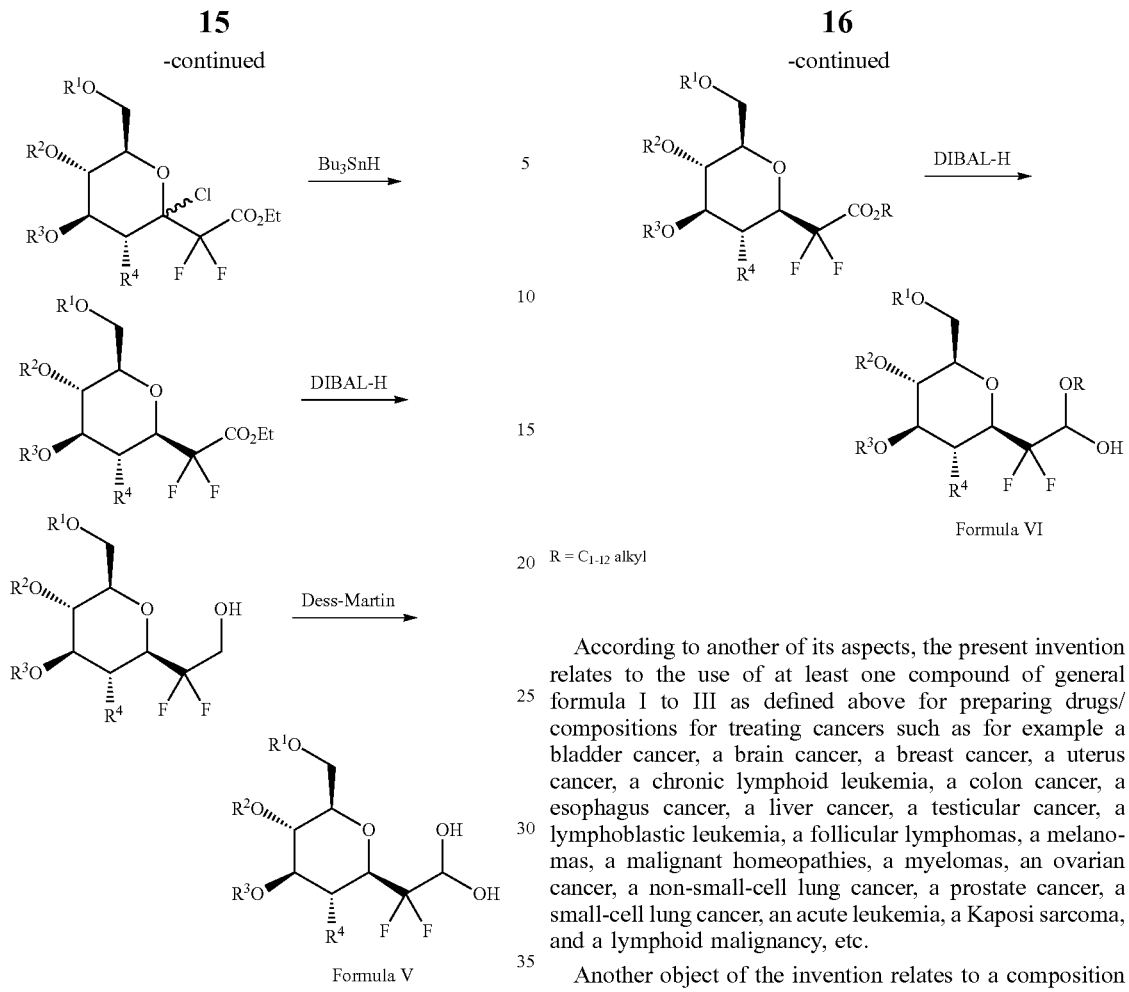

R = $C_{1-12}$ alkyl

Formula VI

The compound of Formula VI is obtained via the following scheme:

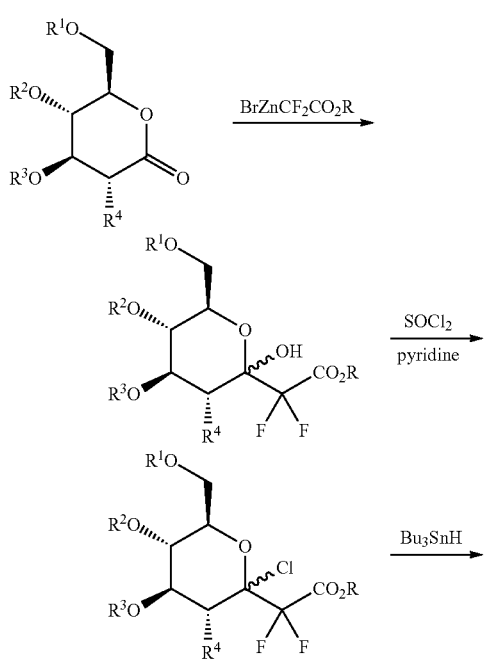

According to another of its aspects, the present invention relates to the use of at least one compound of general formula I to III as defined above for preparing drugs/compositions for treating cancers such as for example a bladder cancer, a brain cancer, a breast cancer, a uterus cancer, a chronic lymphoid leukemia, a colon cancer, a esophagus cancer, a liver cancer, a testicular cancer, a lymphoblastic leukemia, a follicular lymphomas, a melanomas, a malignant homeopathies, a myelomas, an ovarian cancer, a non-small-cell lung cancer, a prostate cancer, a small-cell lung cancer, an acute leukemia, a Kaposi sarcoma, and a lymphoid malignancy, etc.

Another object of the invention relates to a composition comprising at least one compound of formula I to III as defined above.

Of course, the composition according to the invention may comprise compounds of formula I to III as defined above, alone or in a mixture and in any proportions.

In pharmaceutical compositions according to the present invention for administration via an oral, sublingual, inhalation, subcutaneous, intramuscular, intravenous, transdermal, local or rectal route, the active ingredients may be administered as unit administration forms, in a mixture with standard pharmaceutically acceptable supports/carriers.

The suitable unit administration forms include oral forms such as tablets, gelatin capsules, powders, granules and oral solutions or suspensions, topical administration forms, implants, subcutaneous, intramuscular, intravenous, intranasal or intraocular administration forms and rectal administration forms.

In addition, non-toxic and pharmaceutically acceptable excipients, such as distilled water, glucose, starch lactose, talc, vegetable oils, ethylene glycol, etc., may be added.

Compositions may also contain preservatives.

Other active ingredients may be added into the compositions.

The amount of a compound according to the invention and of other possible active ingredients in such compositions may vary depending on the applications, the age, and the weight of the patient, if necessary.

According to another embodiment, there is disclosed a compound of formula (VII) or (VIII):

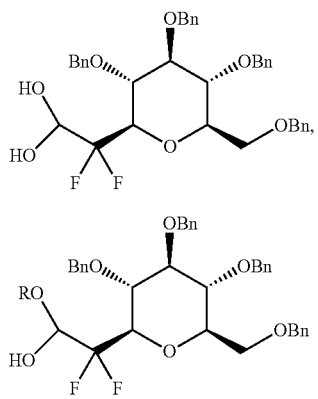

wherein R is a group chosen from methyl, ethyl, butyl, or isopropyl group.

According to another embodiment, there is disclosed the use of a compound of the present invention for the preparation of medicaments for the treatment of cancer.

According to another embodiment, there is disclosed the use of a compound of the present invention for the treatment of cancer.

According to another embodiment, there is disclosed a method of treating a patient afflicted with cancer by administering to the patient a therapeutically effective amount of a compound of the present invention. The method may be effected in combination with radiotherapy, chemotherapy, and/or with one or more other anti-cancer agents.

Non-limiting examples of other anti-cancer agents include but are not limited to, angiogenesis inhibitors, antiproliferative agents, other kinase inhibitors, other receptor tyrosine kinase inhibitors, aurora kinase inhibitors, polo-like kinase inhibitors, bcr-abl kinase inhibitors, growth factor inhibitors, antimitotic agents, alkylating agents, antimetabolites, platinum containing agents, growth factor inhibitors, ionizing radiation, cell cycle inhibitors, topoisomerase inhibitors, biologic response modifiers, immunomodulators, immunologicals, antibodies, hormonal therapies, retinoids/deltoids plant alkaloids, proteasome inhibitors, HSP-90 inhibitors, histone deacetylase inhibitors (HDAC) inhibitors, purine analogs, pyrimidine analogs, MEK inhibitors, CDK inhibitors, ErbB2 receptor inhibitors, mTOR inhibitors, Bcl inhibitors, Mcl inhibitors and combinations thereof as well as other antitumor agents.

Angiogenesis inhibitors include, but are not limited to, EGFR inhibitors, PDGFR inhibitors, VEGFR inhibitors, TIE2 inhibitors, IGFIR inhibitors, matrix metalloproteinase 2 (MMP-2) inhibitors, matrix metalloproteinase 9 (MMP-9) inhibitors, thrombospondin analogs such as thrombospondin-1 and N—Ac-Sar-Gly-Val-D-alloIle-Thr-Nva-He-Arg-Pro-NHCH$_2$CH$_3$ or a salt thereof and analogues of N—Ac-Sar-Gly-Val-D-alloIle-Thr-Nva-Ile-Arg-PrO—NHCH$_2$CH$_3$ such as N—Ac-GlyVal-D-aIle-Ser-Gln-Ile-Arg-ProNHCH$_2$CH$_3$ or a salt thereof.

Examples of EGFR inhibitors include, but are not limited to, Iressa (gefitinib), Tarceva (erlotinib or OSI-774), Icotinib, Erbitux (cetuximab), EMD-7200, ABX-EGF, HR3, IgA antibodies, TP-38 (IVAX), EGFR fusion protein, EGF-vaccine, anti-EGFr immunoliposomes and Tykerb (lapatinib).

Examples of PDGFR inhibitors include, but are not limited to, CP-673,451 and CP-868596.

Examples of VEGFR inhibitors include, but are not limited to, Avastin (bevacizumab), Sutent (sunitinib, SUI 1248), Nexavar (sorafenib, BAY43-9006), regorafenib, CP-547,632, axitinib (AG13736), Apatinib, cabozantinib, Zactima (vandetanib, ZD-6474), AEE788, AZD-2171, VEGF trap, Vatalanib (PTK-787, ZK-222584), Macugen, M862, Pazopanib (GW786034), BC-00016, ABT-869 and angiozyme.

Examples of thrombospondin analogs include, but are not limited to, ABT-510.

Examples of BCL inhibitors include, but not limited to, obatoclax and navitoclax, ABT199.

Examples of aurora kinase inhibitors include, but are not limited to, VX-680, AZD-1152 and MLN-8054. Example of polo-like kinase inhibitors include, but are not limited to, BI-2536.

Examples of bcr-abl kinase inhibitors include, but are not limited to, Gleevec (imatinib), ponatinib nilotinib and Dasatinib (BMS354825).

Examples of platinum containing agents includes, but are not limited to, cisplatin, Paraplatin (carboplatin), eptaplatin, lobaplatin, nedaplatin, Eloxatin (oxaliplatin) or satraplatin.

Examples of mTOR inhibitors includes, but are not limited to, CCI-779, rapamycin, temsirolimus, everolimus, RAD001, INK-128 and ridaforolimus.

Examples of HSP-90 inhibitors includes, but are not limited to, geldanamycin, radicicol, 17-AAG, KOS-953, 17-DMAG, CNF-101, CNF-1010, 17-AAG-nab, NCS-683664, Mycograb, CNF-2024, PU3, PU24FC1, VER49009, IPI-504, SNX-2112 and STA-9090.

Examples of histone deacetylase inhibitors (HDAC) includes, but are not limited to, Suberoylanilide hydroxamic acid (SAHA), MS-275, valproic acid, TSA, LAQ-824, Trapoxin, tubacin, tubastatin, ACY-1215 and Depsipeptide.

Examples of MEK inhibitors include, but are not limited to, PD325901, ARRY-142886, ARRY-438162 and PD98059.

Examples of CDK inhibitors include, but are not limited to, flavopyridol, MCS-5A, CVT-2584, seliciclib (CYC-202, R-roscovitine), ZK-304709, PHA-690509, BMI-1040, GPC-286199, BMS-387,032, PD0332991 and AZD-5438.

Examples of ErbB2 receptor inhibitors include, but are not limited to, CP-724-714, CI-1033, (canertinib), Herceptin (trastuzumab), Omitarg (2C4, petuzumab), TAK-165, GW-572016 (lonafarnib), GW-282974, EKB-569, PI-166, dHER2 (HER2 Vaccine), APC8024 (HER2 Vaccine), anti-HER/2neu bispecific antibody, B7.her2IgG3, AS HER2 trifunctional bispecfic antibodies, mAB AR-209 and mAB 2B-1.

Examples of alkylating agents include, but are not limited to, nitrogen mustard N-oxide, cyclophosphamide, ifosfamide, trofosfamide, Chlorambucil, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, KW-2170, mafosfamide, and mitolactol, carmustine (BCNU), lomustine (CCNU), Busulfan, Treosulfan, Decarbazine and Temozolomide.

Examples of antimetabolites include but are not limited to, methotrexate, 6-mercaptopurine riboside, mercaptopurine, uracil analogues such as 5-fluorouracil (5-FU) alone or in combination with leucovorin, tegafur, UFT, doxifluridine, carmofur, cytarabine, cytarabine, enocitabine, S-I, Alimta (premetrexed disodium, LY231514, MTA), Gemzar (gemcitabine), fludarabine, 5-azacitidine, capecitabine, cladribine, clofarabine, decitabine, eflornithine, ethnylcytidine, cytosine arabinoside, hydroxyurea, TS-I, melphalan, nelarabine, nolatrexed, ocfosate, disodium premetrexed, pentostatin, pelitrexol, raltitrexed, triapine, trimetrexate, vidarabine, vincristine, vinorelbine, mycophenolic acid, tiazofurin, Ribavirin, EICAR, hydroxyurea and deferoxamine.

Examples of topoisomerase inhibiting agents include, but are not limited to, one or more agents selected from the group consisting of aclarubicin, amonafide, belotecan, camptothecin, 10-hydroxycamptothecin, 9-aminocamptothecin, diflomotecan, irinotecan HCL (Camptosar), edotecarin, epirubicin (Ellence), etoposide, exatecan, gimatecan, lurtotecan, orathecin (Supergen), BN-80915, mitoxantrone, pirarbucin, pixantrone, rubitecan, sobuzoxane, SN-38, tafluposide and topotecan.

Examples of antibodies include, but are not limited to, Rituximab, Cetuximab, Bevacizumab, Trastuzimab, specific CD40 antibodies and specific IGFIR antibodies.

Examples of hormonal therapies include, but are not limited to, exemestane (Aromasin), leuprolide acetate, anastrozole (Arimidex), fosrelin (Zoladex), goserelin, doxercalciferol, fadrozole, formestane, tamoxifen citrate (tamoxifen), Casodex, Abarelix, Trelstar, finasteride, fulvestrant, toremifene, raloxifene, lasofoxifene, letrozole, flutamide, bicalutamide, megesterol, mifepristone, nilutamide, dexamethasone, predisone and other glucocorticoids.

Examples of retinoids/deltoids include, but are not limited to, seocalcitol (EB 1089, CB 1093), lexacalcitrol (KH 1060), fenretinide, Aliretinoin, Bexarotene and LGD-1550.

Examples of plant alkaloids include, but are not limited to, vincristine, vinblastine, vindesine and vinorelbine.

Examples of proteasome inhibitors include, but are not limited to, bortezomib (Velcade), MGI 32, NPI-0052 and PR-171.

Examples of immunologicals include, but are not limited to, interferons and numerous other immune enhancing agents. Interferons include interferon alpha, interferon alpha-2a, interferon, alpha-2b, interferon beta, interferon gamma-1a, interferon gamma-1 b (Actimmune), or interferon gamma-nl and combinations thereof. Other agents include filgrastim, lentinan, sizofilan, TheraCys, ubenimex, WF-10, aldesleukin, alemtuzumab, BAM-002, decarbazine, daclizumab, denileukin, gemtuzumab ozogamicin, ibritumomab, imiquimod, lenograstim, lentinan, melanoma vaccine (Corixa), molgramostim, OncoVAC-CL, sargaramostim, tasonermin, tecleukin, thymalasin, tositumomab, Virulizin, Z-100, epratuzumab, mitumomab, oregovomab, pemtumomab (Y-muHMFGI), Provenge (Dendreon), CTLA4 (cytotoxic lymphocyte antigen 4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include krestin, lentinan, sizofrran, picibanil and ubenimex.

Examples of pyrimidine analogs include, but are not limited to, 5-Fluorouracil, Floxuridine, Doxifluridine, Ratitrexed, cytarabine (ara C), Cytosine arabinoside, Fludarabine, and Gemcitabine.

Examples of purine analogs include, but are not limited to, Mercaptopurine and thioguanine.

Examples of immunomodulators include but not limited to, thalidomide and lenalidomide.

Examples of antimitotic agents include, but are not limited to, paclitaxel, docetaxel, ABRAXANE, epothilone D (KOS-862) and ZK-EPO.

Non-limiting examples of cancers that may be treated with the present invention include a bladder cancer, a brain cancer, a breast cancer, a uterus cancer, a chronic lymphoid leukemia, a colon cancer, a esophagus cancer, a liver cancer, a testicular cancer, a lymphoblastic leukemia, a follicular lymphomas, a melanomas, a malignant homeopathies, a myelomas, an ovarian cancer, a non-small-cell lung cancer, a prostate cancer, a small-cell lung cancer, an acute leukemia, a Kaposi sarcoma, and a lymphoid malignancy.

Synthesis

Compounds of the present invention may be made by synthetic chemical processes, examples of which are shown herein below. It is meant to be understood that the order of the steps in the processes may be varied, that reagents, solvents and reaction conditions may be substituted for those specifically mentioned, and that vulnerable moieties may be protected and deprotected, as necessary.

The encountered abbreviations are thus defined as:

| eq.: equivalent | g: gram | Hz: Hertz |
|---|---|---|
| mg: milligram | MHz: megahertz | min: minute |
| mL: milliliter | mmol: millimole | µmol: micromole |
| nmol: nanomole | app: apparent | | s for singlet, bs for broad singlet, d for doublet, t for triplet, q for quartet, m for multiplet or massive, dd for doublet of doublet.

DBU means 1,8-diazabicyclo[5.4.0]undec-7-ene; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino)ethane; DMSO means dimethylsulfoxide; dppb means 1,4-bis(diphenylphosphino)butane; dppe means 1,2-bis(diphenylphosphino)ethane; dppf means 1,1'-bis(diphenylphosphino)ferrocene; dppm means 1,1'-bis(diphenylphosphino)methane; DIAD means diisopropylazodicarboxylate; EDCI means 1-(3-dimethylaminopropyl)-3-ethylcarbodiimide; HATU means 2-(7-Aza-1 H-benzotriazole-1-yl)-1,1,3,3-tetramethyluronium hexafluorophosphate; HMPA means hexamethyiphosphoramide; IPA means isopropyl alcohol; LDA means lithium diisopropylamide; LHMDS means lithium bis(hexamethyldisilylamide); LAH means lithium aluminum hydride; NCS means N-chlorosuccinimide; PyBOP means benzotriazol-1-yloxytripyrrolidinophosphonium hexafluorophosphate; TDA-I means tris(2-(2-methoxyethoxy)ethyl)amine; DCM means dichloromethame; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine, RBF means round-bottom flask.

The characteristics of the apparatuses used for carrying out analyses of all the compounds described in the present application are indicated below:

The $^1H$, $^{13}C$, $^{19}F$ NMR spectra are recorded on Bruker Corporation™ spectrometers. In $^1H$ and $^{13}C$ NMR, tetramethylsilane is used as an internal reference. In $^{19}F$ NMR, the external reference is fluorotrichloromethane $CFCl_3$. The chemical displacements are expressed in parts per million (ppm), the coupling constants J in Hertz (Hz).

The present invention will be more readily understood by referring to the following examples which are given to illustrate the invention rather than to limit its scope.

Example 1

Preparation of (5R,5aR,8aS,9S)-9-((2,2-difluoro-2-((2R,3R,4S,5S,6R)-3,4,5-trihydroxy-6-(hydroxymethyl)tetrahydro-2H-pyran-2-yl)ethyl)amino)-5-(4-hydroxy-3,5-dimethoxyphenyl)-5,5a,8a,9-tetrahydrofuro[3',4':6,7]naphtho[2,3-d][1,3]dioxol-6(8H)-one

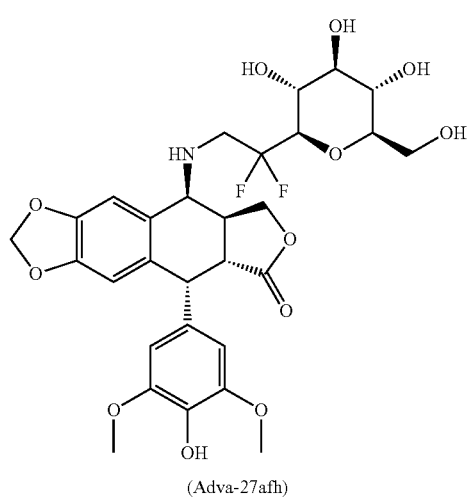 [SMILES: COc1cc([C@@H]2c3cc4c(cc3[C@@H](NCC(F)(F)[C@@H]3O[C@H](CO)[C@@H](O)[C@H](O)[C@H]3O)[C@H]3COC(=O)[C@H]23)OCO4)cc(OC)c1O]

(Adva-27afh)

Method A

Step 1 2R,3R,4S,5R)-3,4,5-tris(benzyloxy)-2-(benzyloxymethyl)-6-methoxytetrahydro-2H-pyran

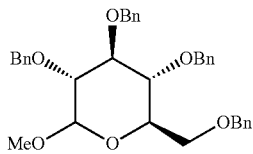 [SMILES: COC1O[C@H](COCc2ccccc2)[C@@H](OCc2ccccc2)[C@H](OCc2ccccc2)[C@H]1OCc1ccccc1]

To a solution of (2R,3S,4S,5R)-2-(hydroxymethyl)-6-methoxytetrahydro-2H-pyran-3,4,5-triol (10 g, 51.5 mmol, 1.0 equiv) and tetrabutylammonium iodide (0.95 g, 2.575 mmol, 5 mol %) in DMF (anhydrous, 500 mL) is added sodium hydride (12.4 g, 60 wt % in oil, 309 mmol, 6.0 equiv) portionwise at 0° C. under nitrogen (be careful, the addition time is about 2 hrs). After addition of NaH, the mixture is stirred at 0° C. for 30 min and at room temperature for 60 min. Benzyl bromide (36.75 mL, 309 mmol, 6.0 equiv) is added by addition funnel. The mixture is then stirred at room temperature for 20 hrs. The reaction is quenched by addition of MeOH (30 mL) slowly (be careful, $H_2$ generated) at 0° C. A saturated solution of $NH_4Cl$ (200 mL) and $H_2O$ (600 mL) are then added. The aqueous phase is extracted with ether (3×500 mL). The combined ethereal solution is washed with brine (200 mL), dried over anhydrous $Na_2SO_4$, concentrated to give 40 g of crude (2R,3R,4S,5R)-3,4,5-tris(benzyloxy)-2-(benzyloxymethyl)-6-methoxytetrahydro-2H-pyran as a pale yellow oil which is submitted for next reaction without further purification.

LC-MS: 577.3 (M+Na+, ESI)

Step 2 (3R,4S,5R,6R)-3,4,5-tris(benzyloxy)-6-((benzyloxy)methyl)tetrahydro-2H-pyran-2-ol

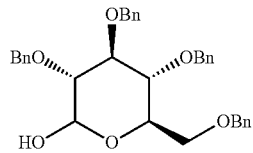

To a solution of the crude (2R,3R,4S,5R)-3,4,5-tris(benzyloxy)-2-(benzyloxymethyl)-6-methoxytetrahydro-2H-pyran (10 g of crude) in AcOH (100 mL) is added a solution of $H_2SO_4$ (3.0 M, 15 mL). The solution is heated to 110° C. (oil bath) and stirred at this temperature for 1.0 h. TLC indicated that starting material is consumed. Hexane (60 mL) is added. The pale yellow mixture is allowed to cool to room temperature. $H_2O$ (50 mL) is added when the solution is cooled to about 40-50° C. A white solid is precipitated, and it is stirred at room temperature for 30 min, then filtered, eluted with Hexane (30 mL) and $H_2O$ (200 mL) to afford 3.28 g (47%) of the title compound as a white solid.

LC-MS: 563.3 (M+Na+, ESI).

Step 3 (3R,4S,5R,6R)-3,4,5-tris(benzyloxy)-6-((benzyloxy)methyl)tetrahydro-2H-pyran-2-one

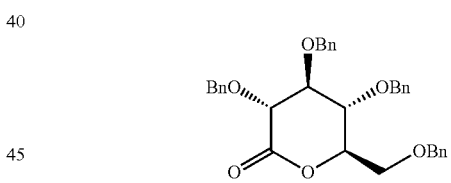

To a solution of (3R,4S,5R,6R)-3,4,5-tris(benzyloxy)-6-(benzyloxymethyl)tetrahydro-2H-pyran-2-ol (18 g, 33.3 mmol, 1.0 equiv) in DMSO (120 mL) is added acetic anhydride (80 mL) under nitrogen. The solution is stirred at room temperature overnight (about 18 hrs). After TLC indicated that starting material is consumed, $H_2O$ (200 mL) is added, followed by addition of $Na_2CO_3$ (20 g) carefully at 0° C. and $H_2O$ (200 mL). The aqueous phase is extracted with ether (3×250 mL). The combined ethereal solution is washed with $H_2O$ (2×100 mL), saturated $NaHCO_3$ (100 mL) and brine (100 mL), dried over anhydrous $Na_2SO_4$, concentrated to give the residue which is purified by CombiFlash® (120 g silicagel, EtOAc/Hex=0-30%) to give 16.37 g (91%) of the title compound as a colorless sticky oil.

LC-MS: 561.3 (M+Na+, ESI).

Step 4 ethyl 2,2-difluoro-2-((3R,4S,5R,6R)-3,4,5-tris(benzyloxy)-6-((benzyloxy)methyl)-2-hydroxytetrahydro-2H-pyran-2-yl)acetate

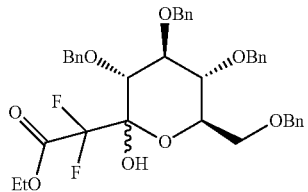 [SMILES: CCOC(=O)C(F)(F)C1(O)O[C@H](COCc2ccccc2)[C@@H](OCc2ccccc2)[C@H](OCc2ccccc2)[C@H]1OCc1ccccc1]

To a suspension of Zn/Cu couple (16.15 g, 0.247 mol, 7.0 equiv) in THF (dry, 200 mL) is added a solution of (3R,4S,5R,6R)-3,4,5-tris(benzyloxy)-6-(benzyloxymethyl)tetrahydro-2H-pyran-2-one (19 g, 35.275 mmol, 1.0 equiv) and ethyl bromodifluoroacetate (14.5 mL, 0.106 mol, 3.0 equiv) in THF (dry, 200 mL) dropwise at reflux under nitrogen. After addition, the mixture is refluxed for 3 hrs. LC-MS indicated desired product observed and no starting material left. The mixture is cooled to room temperature and a solution of HCl (1.0 M, 400 mL) is added. DCM (200 mL) is then added. The layers are separated and the aqueous phase is extracted with DCM (2×150 mL). The combined organic phase is dried over anhydrous $Na_2SO_4$, concentrated to give the residue which is purified by CombiFlash® (120 g silicagel, EtOAc/Hex=0-30%) to afford 17.8 g (76%) of the title compound as a colorless sticky oil.

LC-MS: 685.3 (M+Na$^+$, ESI).

Step 5 ethyl 2,2-difluoro-2-((3R,4S,5R,6R)-3,4,5-tris(benzyloxy)-6-((benzyloxy)methyl)-2-chlorotetrahydro-2H-pyran-2-yl)acetate

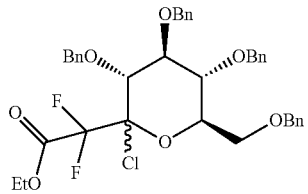 [SMILES: CCOC(=O)C(F)(F)C1(Cl)O[C@H](COCc2ccccc2)[C@@H](OCc2ccccc2)[C@H](OCc2ccccc2)[C@H]1OCc1ccccc1]

To a solution of ethyl 2,2-difluoro-2-((3R,4S,5R,6R)-3,4,5-tris(benzyloxy)-6-(benzyloxymethyl)-2-hydroxytetrahydro-2H-pyran-2-yl)acetate (13.63 g, 20.567 mmol, 1.0 equiv) in DCM (dry, 170 mL) is added pyridine (2.5 mL, 30.85 mmol, 1.5 equiv) under $N_2$. The solution is cooled to 0° C. with an external ice-bath. Thionyl chloride (2.25 mL, 30.85 mmol, 1.5 equiv) is then added dropwise and maintained the temperature not over 5° C. After addition, the solution is stirred for 10 min and ice-bath is removed. The solution is allowed to warm to room temperature (about 20 min). TLC indicated that starting material is consumed. A solution of HCl (1.0 N, 150 mL) is added. DCM is added (380 mL). The layers are separated. The organic layer is washed with a saturated solution of $NaHCO_3$ (150 mL), $H_2O$ (150 mL) and dried over anhydrous $Na_2SO_4$, concentrated to give the yellow oil which is purified by CombiFlash® (120 g silicagel, EtOAc/Hex=0-25%) to afford 8.34 g (59%) of the title compound as a colorless sticky oil.

LC-MS: 703 (M+Na$^+$, ESI)

Step 6 ethyl 2,2-difluoro-2-((3R,4S,5R,6R)-3,4,5-tris(benzyloxy)-6-((benzyloxy)methyl)tetrahydro-2H-pyran-2-yl)acetate

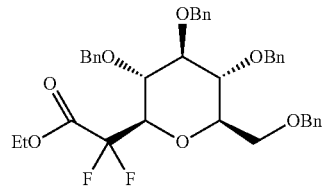 [SMILES: CCOC(=O)C(F)(F)[C@@H]1O[C@H](COCc2ccccc2)[C@@H](OCc2ccccc2)[C@H](OCc2ccccc2)[C@H]1OCc1ccccc1]

To a solution of ethyl 2,2-difluoro-2-((3R,4S,5R,6R)-3,4,5-tris(benzyloxy)-6-(benzyloxymethyl)-2-chlorotetrahydro-2H-pyran-2-yl)acetate (7.21 g, 10.585 mmol, 1.0 equiv) in toluene (dry, 60 mL) is added tributyltin hydride (4.27 mL, 15.88 mmol, 1.5 equiv) and (E)-1,1'-(diazene-1,2-diyl)dicyclohexanecarbonitrile (129 mg, 0.529 mmol, 5 mol %) under $N_2$. The solution is heated to reflux and refluxed for 1 h. LC-MS indicated that starting material is consumed. It is concentrated to give the residue which is purified by CombiFlash® (120 g silicagel, EtOAc/Hex=0-25%) to afford 6.13 g (90%) of the title compound as a colorless sticky oil.

$^{19}$FNMR (CDCl3, 376 MHz): −115.84 (dd, $J_{F-H}$12.05, $J_{F-F}$260.11), −118.84 (dd, $J_{F-H}$9.79, $J_{F-F}$258.60)

LC-MS: 669.3 (M+Na$^+$, ESI)

Step 7 2,2-difluoro-2-((2R,3R,4S,5R,6R)-3,4,5-tris(benzyloxy)-6-(benzyloxymethyl)tetrahydro-2H-pyran-2-yl)acetic acid

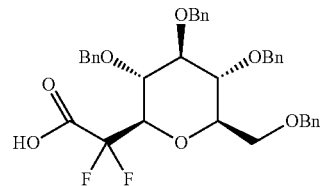 [SMILES: O=C(O)C(F)(F)[C@@H]1O[C@H](COCc2ccccc2)[C@@H](OCc2ccccc2)[C@H](OCc2ccccc2)[C@H]1OCc1ccccc1]

To a solution of (2R,3R,4S,5R,6R)-3,4,5-tris(benzyloxy)-2-(benzyloxymethyl)-6-(2-(ethylperoxy)-1,1-difluoroethyl)tetrahydro-2H-pyran (5 g, 7.73 mmol, 1.0 equiv) in EtOH (150 mL) is added a solution of LiOH (2.0 M, 8.0 mL, 7.8 mL, 15.46 mmol, 2.0 equiv) at room temperature under nitrogen. The mixture is stirred at room temperature overnight (18 hrs). TLC indicated that starting material is consumed. The mixture is concentrated to give the residue which is dissolved in DCM (100 mL). A solution of HCl (1.0 N, 50 mL) is added and stirred for 10 min. The layers are separated, and aqueous phase is extracted with DCM (3×100 mL). The combined organic phase is dried over anhydrous sodium sulfate and concentrated to afford 4.66 g (97%) of the title compound as a colorless sticky oil.

$^{19}$FNMR (CDCl3, 376 MHz): −115.00 (dd, $J_{F-H}$9.0, $J_{F-F}$261.62), −118.88 (dd, $J_{F-H}$11.67, $J_{F-F}$261.24)

LC-MS: 641.3 (M+Na$^+$, ESI)

Step 8 2,2-difluoro-2-((2R,3R,4S,5R,6R)-3,4,5-tris (benzyloxy)-6-(benzyloxymethyl)tetrahydro-2H-pyran-2-yl)ethanol

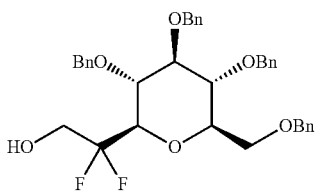 [SMILES: OCC(F)(F)[C@@H]1O[C@H](COCc2ccccc2)[C@@H](OCc2ccccc2)[C@H](OCc2ccccc2)[C@H]1OCc1ccccc1]

To a solution of 2,2-difluoro-2-((3R,4S,5R,6R)-3,4,5-tris (benzyloxy)-6-(benzyloxymethyl)tetrahydro-2H-pyran-2-yl)acetic acid (1.54 g, 2.49 mmol, 1.0 equiv) in THF (dry, 5 mL) is added a solution of $BH_3SMe_2$ (2.0 M, 0.6 mL, 5.0 mmol, 2.0 equiv) at 0° C. and it is stirred and allowed to warm to RT overnight. TLC indicated that no reaction. The solution is heated to reflux for 3 hrs. TLC indicated that starting material is not consumed. $BH_3SMe_2$ (2.0 mL) is added. The solution is refluxed overnight. TLC indicated that starting material is consumed. The solution is cooled to RT and is quenched by addition of a solution of HCl (1.0 M, 10 mL), saturated $NH_4Cl$ (20 mL), $H_2O$ (20 mL). The mixture is stirred at room temperature for 10 min, extracted with EtOAc (4×50 mL). The combined organic solution is washed with brine (50 mL), dried over anhydrous $Na_2SO_4$, concentrated to give residue which is purified by Combi-Flash® (40 g silicagel, EtOAc/Hexane=0-40%) to afford 1.44 g (95.7%) of the title compound as a colorless oil.

LC-MS: 627.3 ($M+Na^+$, ESI)

Step 9 2,2-difluoro-2-((2R,3R,4S,5R,6R)-3,4,5-tris (benzyloxy)-6-(benzyloxymethyl)tetrahydro-2H-pyran-2-yl)ethane-1,1-diol

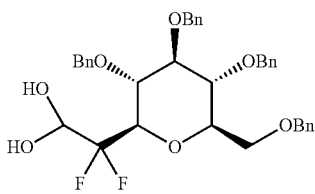

To a solution of 2,2-difluoro-2-((2R,3R,4S,5R,6R)-3,4,5-tris(benzyloxy)-6-(benzyloxymethyl)tetrahydro-2H-pyran-2-yl)ethanol (1.44 g, 2.38 mmol, 1.0 equiv) in DMSO (dry, 12 mL) is added IBX (1.39 g, 4.76 mmol, 2.0 equiv). The mixture is stirred at room temperature and became clear solution after stirring about 30 min. The solution is stirred at room temperature for 24 hrs. TLC indicated that reaction is not completed, but desired product observed. $H_2O$ (10 mL) is added. The mixture is stirred at room temperature for 20 min. $H_2O$ (100 mL) is added, and the aqueous phase is extracted with EtOAc (4×80 mL). The combined organic solution is washed with $H_2O$ (2×50 mL), brine (50 mL), dried over anhydrous $Na_2SO_4$, concentrated to give residue which is purified by CombiFlash® (50 g silicagel, EtOAc/Hexane=0-50%) to afford 560 mg (38%) of the title compound and recovered 267 mg of the starting material as a colorless oil.

LC-MS: 643.3 ($M+Na^+$, ESI)

Step 10 (5R,5aR,8aS,9S)-9-((2,2-difluoro-2-((2R,3R,4S,5R,6R)-3,4,5-tris(benzyloxy)-6-((benzyloxy) methyl)tetrahydro-2H-pyran-2-yl)ethyl)amino)-5-(4-hydroxy-3,5-dimethoxyphenyl)-5,5a,8a,9-tetrahydrofuro[3',4':6,7]naphtho[2,3-d][1,3]dioxol-6 (8H)— one

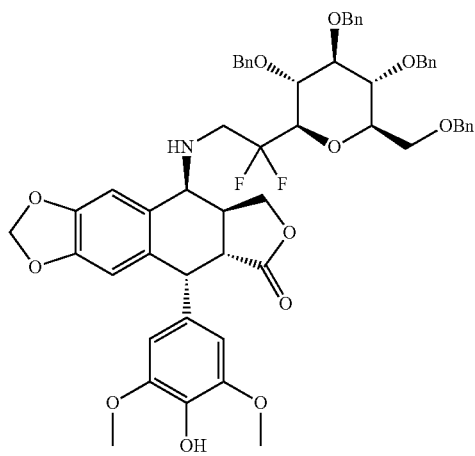

To a suspension of (5R,5aR,8aS,9S)-9-amino-5-(4-hydroxy-3,5-dimethoxyphenyl)-5,5a,8a,9-tetrahydrofuro[3',4': 6,7]naphtho[2,3-d][1,3]dioxol-6(8H)-one (45 mg, 0.113 mmol, 1.0 equiv. prepared according to U.S. Pat. No. 8,236,935) and sodium cyanoborohydride (15 mg, 0.237 mmol, 2.1 equiv) in DCM (dry, 2.0 mL) is added TFA (108 µL, 1.45 mmol, 12.85 equiv) by syringe dropwise at 0° C. under nitrogen. A solution of 2,2-difluoro-2-((2R,3R,4S,5R, 6R)-3,4,5-tris(benzyloxy)-6-(benzyloxymethyl)tetrahydro-2H-pyran-2-yl)ethane-1,1-diol (140 mg, 0.225 mmol, 2.0 equiv) in DCM (3.0 mL) is then added dropwise. The suspension is stirred at 0° C. and allowed to warm to room temperature gradually. The mixture is stirred at room temperature for 40 hrs. TLC indicated that starting material is consumed. A solution of saturated $NaHCO_3$ (20 mL) is added dropwise and $H_2O$ (10 mL). DCM (20 mL) is added. The mixture is stirred at room temperature for 30 min. The layers are separated. The aqueous phase is extracted with DCM (3×30 mL). The combined organic solution is passed through a pad of Celite®, eluted with DCM (30 mL). The combined organic solution is dried over anhydrous $Na_2SO_4$, concentrated to give residue which is purified by Combi-Flash® (12 g silicagel, EtOAc/Hexane=0-60%) to afford 56 mg (50%) of the title compound as a white solid.

MS: 986.0 ($M^+$+H, EI)

Step 11 (5R,5aR,8aS,9S)-9-((2,2-difluoro-2-((2R, 3R,4S,5S,6R)-3,4,5-trihydroxy-6-(hydroxymethyl) tetrahydro-2H-pyran-2-yl)ethyl)amino)-5-(4-hydroxy-3,5-dimethoxyphenyl)-5,5a,8a,9-tetrahydrofuro[3',4':6,7]naphtho[2,3-d][1,3]dioxol-6(8H)— one

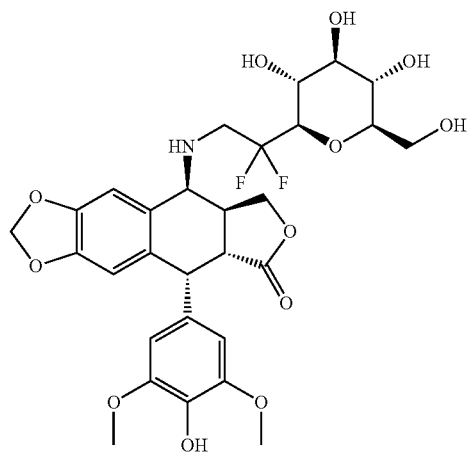 [SMILES: COc1cc([C@@H]2c3cc4c(cc3[C@@H](NCC(F)(F)[C@@H]3O[C@H](CO)[C@@H](O)[C@H](O)[C@H]3O)[C@H]3COC(=O)[C@H]23)OCO4)cc(OC)c1O]

To a solution of the product of Step 10 (88 mg, 89 μmol, 1.0 equiv) in MeOH (5.0 mL) is added a Pd—C(10% on activated carbon, 90 mg) in one portion. The mixture is sonicated under $H_2$ balloon for 4 hrs. LC-MS indicated that starting material is not consumed and Pd—C(30 mg) is added. The mixture is sonicated for another 2 hrs. The mixture is filtered through a pad of Celite® to remove the catalyst, eluted with MeOH (20 mL). The combined methanol solution is concentrated to give the crude which is purified by CombiFlash® (10 g silicagel column, drying loading, MeOH/DCM=0-20%) to give 32 mg (57%) of the title compound as a white solid.

LC-MS: 626.3 ($M^+$+H, ESI).

Method B

Step 1 1-ethoxy-2,2-difluoro-2-((2R,3R,4S,5R,6R)-3,4,5-tris(benzyloxy)-6-((benzyloxy)methyl)tetrahydro-2H-pyran-2-yl)ethanol

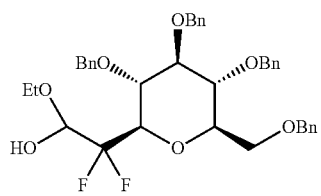 [SMILES: CCOC(O)C(F)(F)[C@@H]1O[C@H](COCc2ccccc2)[C@@H](OCc2ccccc2)[C@H](OCc2ccccc2)[C@H]1OCc1ccccc1]

To a solution of ethyl 2,2-difluoro-2-((2R,3R,4S,5R,6R)-3,4,5-tris(benzyloxy)-6-(benzyloxymethyl)tetrahydro-2H-pyran-2-yl)acetate (200 mg, 0.309 mmol, 1.0 equiv) in toluene (dry, 8 mL) is added a solution of diisobutylaluminium hydride (1.0 M in toluene, 0.464 mL, 0.464 mmol, 1.5 equiv) dropwise at −78° C. under nitrogen. The mixture is stirred at this temperature for 1 hr and is quenched by addition of EtOH (anhydrous 3.0 mL) dropwise at −78° C. The solution is allowed to warm to room temperature and a solution of Rochelle's solution (20 wt %, 20 mL) is added. The mixture is vigorously stirred for 1 hr. EtOAc (25 mL) is added. The layers are separated. The aqueous phase is extracted with EtOAc (3×25 mL). The combined organic phase is washed with brine (30 mL), dried over anhydrous $Na_2SO_4$, concentrated to give 200 mg (yield 100%) of the crude 1-ethoxy-2,2-difluoro-2-((2R,3R,4S,5R,6R)-3,4,5-tris(benzyloxy)-6-(benzyloxymethyl)tetrahydro-2H-pyran-2-yl)ethanol as a colorless sticky oil. It is employed for the next reaction without further purification.

MS: 671.3 ($M^+$+Na, ESI).

Step 2 (5R,5aR,8aS,9S)-9-azido-5-(4-(benzyloxy)-3,5-dimethoxyphenyl)-5,5a,8a,9-tetrahydrofuro[3',4':6,7]naphtho[2,3-d][1,3]dioxol-6(8H)-one

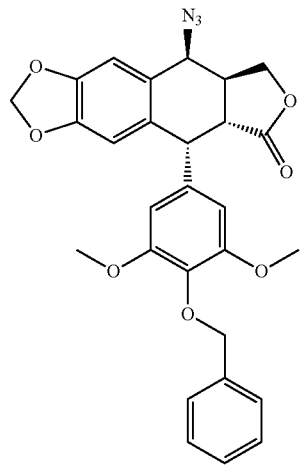 [SMILES: COc1cc([C@@H]2c3cc4c(cc3[C@@H](N=[N+]=[N-])[C@H]3COC(=O)[C@H]23)OCO4)cc(OC)c1OCc1ccccc1]

A mixture of (5R,5aR,8aS,9S)-9-azido-5-(4-hydroxy-3,5-dimethoxyphenyl)-5,5a,8a,9-tetrahydrofuro[3',4': 6,7]naphtho[2,3-d][1,3]dioxol-6(8H)-one (0.5 g, 1.18 mmol), benzyl bromide (0.26 g, 1.52 mmol) and $K_2CO_3$ (0.42 g, 3.04 mmol) in 20 mL of MeCN is heated to reflux overnight. The mixture is diluted with EtOAc and filtered through a silica gel pad. The solvent is evaporated and the residue is purified by Combiflash® (0-60% EtOAc/hexane) to afford the desired (0.47 g, 78%).

MS (+ESI): m/e ($M+H^+$)=516.2.

Step 3 (5R,5aR,8aS,9S)-9-amino-5-(4-(benzyloxy)-3,5-dimethoxyphenyl)-5,5a,8a,9-tetrahydrofuro[3',4':6,7]naphtho[2,3-d][1,3]dioxol-6(8H)-one

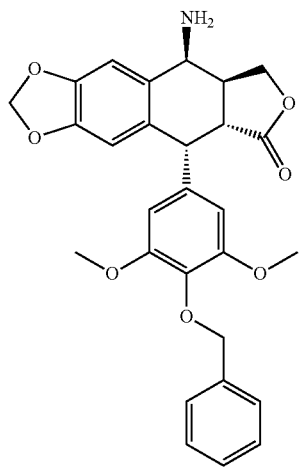 [SMILES: COc1cc([C@@H]2c3cc4c(cc3[C@@H](N)[C@H]3COC(=O)[C@H]23)OCO4)cc(OC)c1OCc1ccccc1]

A mixture of (5R,5aR,8aS,9S)-9-azido-5-(4-(benzyloxy)-3,5-dimethoxyphenyl)-5,5a,8a,9-tetrahydrofuro[3',4':6,7]naphtho[2,3-d][1,3]dioxol-6(8H)-one (0.47 g, 0.91 mmol) and PPh$_3$ (0.252 g, 0.96 mmol) in 20 mL of THF/water (10:1) is heated to reflux overnight. The solvent is evaporated and the residue is purified by Combiflash® (0-60% EtOAc/hexane) to afford the desired (0.38 g, 85%). $^1$H NMR (CDCl$_3$, 400 MHz): 7.40 (d, 2H), 7.26-7.36 (m, 3H), 6.80 (s, 1H), 6.51, (s, 1H), 6.31 (s, 2H), 5.97 (d, 2H), 4.96 (s, 2H), 4.57 (d, 1H), 4.3-4.35 (m, 2H), 4.21 (d, 1H), 3.71 (s, 6H), 3.30 (dd, 1H), 2.78-2.90 (m, 1H).

Step 4 (5R,5aR,8aS,9S)-5-(4-(benzyloxy)-3,5-dimethoxyphenyl)-9-((2,2-difluoro-2-((2R,3R,4S,5R,6R)-3,4,5-tris(benzyloxy)-6-((benzyloxy)methyl)tetrahydro-2H-pyran-2-yl)ethyl)amino)-5,5a,8a,9-tetrahydrofuro[3',4':6,7]naphtho[2,3-d][1,3]dioxol-6(8H)-one

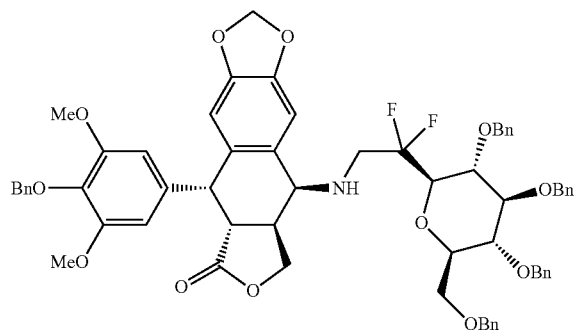 [SMILES: COc1cc([C@@H]2c3cc4c(cc3[C@@H](NCC(F)(F)[C@@H]3O[C@H](COCc5ccccc5)[C@@H](OCc5ccccc5)[C@H](OCc5ccccc5)[C@H]3OCc3ccccc3)[C@H]3COC(=O)[C@H]23)OCO4)cc(OC)c1OCc1ccccc1]

The 2-neck-RBF (25 mL) is equipped with Dean-Stark trap and condenser under nitrogen. 1-ethoxy-2,2-difluoro-2-((2R,3R,4S,5R,6R)-3,4,5-tris(benzyloxy)-6-(benzyloxymethyl)tetrahydro-2H-pyran-2-yl)ethanol (200 mg, 0.308 mmol, 1.0 equiv) and (5R,5aR,8aS,9S)-9-amino-5-(4-(benzyloxy)-3,5-dimethoxyphenyl)-5,5a,8a,9-tetrahydrofuro[3',4':6,7]naphtho[2,3-d][1,3]dioxol-6(8H)-one (151 mg, 0.308 mmol, 1.0 equiv) and 4-methylbenzenesulfonic acid monohydrate (12 mg, 0.031 mmol, 20 mol %) are added. After addition of toluene (dry, 8.0 mL), the mixture is heated to reflux for 18 hrs. The mixture is then concentrated to remove the solvent to give a yellow foam solid (MS: 1073.5). THF (dry, 8 mL) is added. Followed by addition of AcOH (80 µL, 1.4 mmol, 4.5 equiv) and sodium cyanoboronhydride (80 mg, 1.27 mmol, 4.1 equiv) at 0° C. under N$_2$. The clear yellow solution is stirred at 0° C. for 60 min and is then stirred at room temperature for 2 hr. A saturated solution of NaHCO$_3$ (20 mL) is added. The mixture is extracted with DCM (5×25 mL). The combined organic solution is dried over anhydrous Na$_2$SO$_4$, concentrated to give residue which is purified by CombiFlash® (12 g silicagel, EtOAc/Hexane=0-50%) to afford 190 mg (57%) of title compound as a white solid.

MS: 1075.5

Step 5 (5R,5aR,8aS,9S)-9-((2,2-difluoro-2-((2R,3R,4S,5S,6R)-3,4,5-trihydroxy-6-(hydroxymethyl)tetrahydro-2H-pyran-2-yl)ethyl)amino)-5-(4-hydroxy-3,5-dimethoxyphenyl)-5,5a,8a,9-tetrahydrofuro[3',4':6,7]naphtho[2,3-d][1,3]dioxol-6(8H)-one

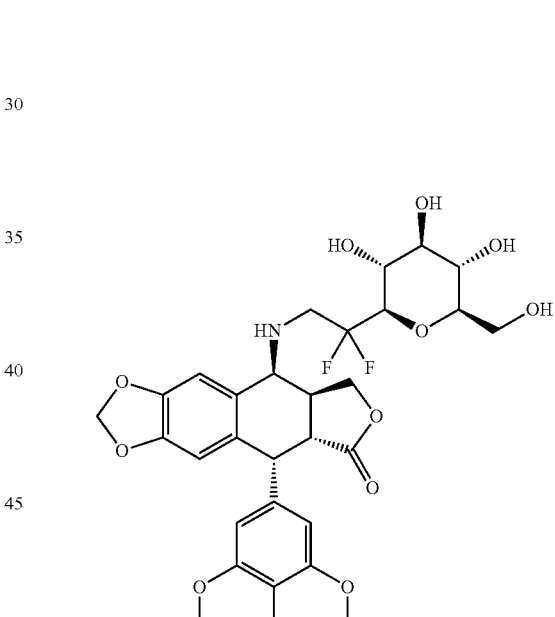

To a solution of the product of Step 2 (190 mg, 0.177 mmol, 1.0 equiv) in MeOH (10 mL) is added Pd—C(105 mg, 10 wt % on the activated carbon). The mixture is then sonicated under H$_2$ balloon for 3.5 hrs. The mixture is passed through a pad of Celite® and eluted with MeOH (15 mL). The combined methanol solution is concentred to dryness which is purified by CombiFlash® (12 g silicagel, MeOH/DCM=0-20%) to afford 88 mg (yield 79.7%) of title compound as a white solid.

MS: 626.3 (M$^+$+Na, ESI)

Example 2

Preparation of (5R,5aR,8aS,9S)-9-((2,2-difluoro-2-((2R,3R,4S,5S,6R)-3,4,5-trihydroxy-6-(hydroxymethyl)tetrahydro-2H-pyran-2-yl)ethyl)amino)-5-(3,4,5-trimethoxyphenyl)-5,5a,8a,9-tetrahydrofuro[3',4':6,7]naphtho[2,3-d][1,3]dioxol-6(8H)-one

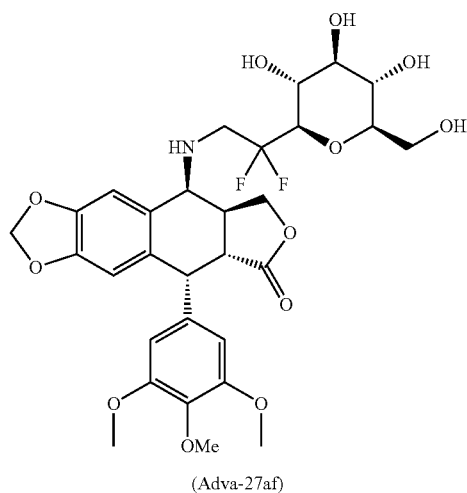 [SMILES: COc1cc([C@@H]2c3cc4c(cc3[C@@H](NCC(F)(F)[C@@H]3O[C@H](CO)[C@@H](O)[C@H](O)[C@H]3O)[C@H]3COC(=O)[C@H]23)OCO4)cc(OC)c1OC]

(Adva-27af)

Step 1 ((5R,5aR,8aS,9S)-9-((2,2-difluoro-2-((2R,3R,4S,5R,6R)-3,4,5-tris(benzyloxy)-6-((benzyloxy)methyl)tetrahydro-2H-pyran-2-yl)ethyl)amino)-5-(3,4,5-trimethoxyphenyl)-5,5a,8a,9-tetrahydrofuro[3',4':6,7]naphtho[2,3-d][1,3]dioxol-6(8H)-one

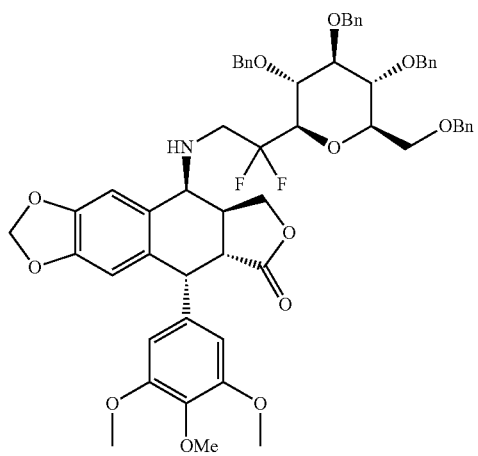 [SMILES: COc1cc([C@@H]2c3cc4c(cc3[C@@H](NCC(F)(F)[C@@H]3O[C@H](COCc5ccccc5)[C@@H](OCc5ccccc5)[C@H](OCc5ccccc5)[C@H]3OCc3ccccc3)[C@H]3COC(=O)[C@H]23)OCO4)cc(OC)c1OC]

The RBF (25 mL), condenser and Dean-Stark trap are dried in oven and cooled to room temperature under nitrogen. 2,2-difluoro-2-((2R,3R,4S,5R,6R)-3,4,5-tris(benzyloxy)-6-(benzyloxymethyl)tetrahydro-2H-pyran-2-yl)ethane-1,1-diol (120 mg, 0.193 mmol, 1.0 equiv) and using (5R,5aR,8aS,9S)-9-amino-5-(3,4,5-trimethoxyphenyl)-5,5a,8a,9-tetrahydrofuro[3',4':6,7]naphtho[2,3-d][1,3]dioxol-6(8H)-one (80 mg, 0.193 mmol, 1.0 equiv, prepared according to U.S. Pat. No. 8,236,935) and 4-methylbenzenesulfonic acid (5 mg, 19 μmmol, 10 mol %) are added. After addition of toluene (dry, 5.0 mL), the mixture is heated to reflux (oil bath 130-132° C.) overnight (16 hrs). TLC indicated that reaction is almost completed (aldehyde hydrate as reference). The mixture is concentrated to remove the solvent to give the yellow solid. THF (dry, 5 mL) is added. Followed by addition of AcOH (45 μL) and sodium cyanoboronhydride (45 mg, 0.716 mmol. 3.7 equiv) at 0° C. under $N_2$. The clear solution is formed after addition of $NaBH_3CN$, and stirred at 0° C. for 45 min. The mixture is then stirred at room temperature for 2 hr. Additional AcOH (50 μL) and $NaBH_3CN$ (50 mg) are added. It is stirred at room temperature overnight. $H_2O$ (30 mL) and saturated $NaHCO_3$ (20 mL) are added, and the aqueous phase is extracted with DCM (5×25 mL). The combined organic solution is dried over anhydrous $Na_2SO_4$, concentrated to give residue which is purified by CombiFlash® (12 g silicagel, EtOAc/Hexane=0-50%) to afford 157 mg (81%) of title compound as a white solid.

LC-MS: 1000 ($M^+$+H), 1022 ($M^+$+Na$^+$)

Step 2 (5R,5aR,8aS,9S)-9-((2,2-difluoro-2-((2R,3R,4S,5S,6R)-3,4,5-trihydroxy-6-(hydroxymethyl)tetrahydro-2H-pyran-2-yl)ethyl)amino)-5-(3,4,5-trimethoxyphenyl)-5,5a,8a,9-tetrahydrofuro[3',4':6,7]naphtho[2,3-d][1,3]dioxol-6(8H)-one

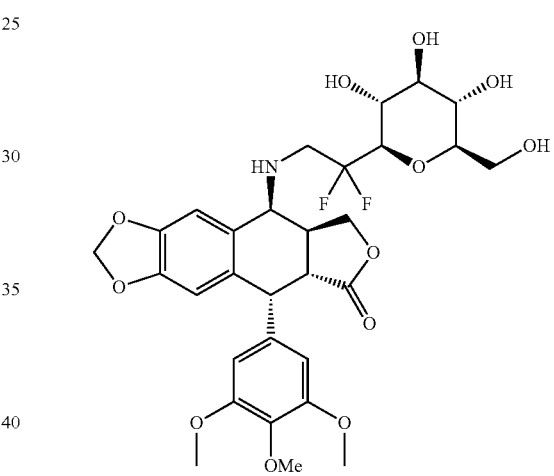

To a solution of the product of Step 1 (157 mg, 157 pmmol, 1.0 equiv) in MeOH/THF (6.0/2.0 mL) is added a Pd—C(10% Pd on activated carbon, 80 mg) in one portion. The mixture is stirred at room temperature under $H_2$ balloon for 40 hrs. LC-MS indicated that starting material is not consumed although desired product is observed. Additional Pd—C catalyst (100 mg) is added. It is stirred at room temperature for 4 days. It is filtered through a pad of Celite® to remove the catalyst, eluted with MeOH (10 mL). The combined methanol solution is concentrated to give the crude which is purified by CombiFlash® (12 g silicagel column, MeOH/DCM=0-20%) to give 57.7 mg (57%) of the title compound as a white solid.

LC-MS: 640.3 ($M^+$+H, ESI)

Example 3

Biochemical Evaluation of Compounds of Examples 1 & 2

3.1—Human Topoisomerase II DNA Decatenation Assays
(1). Assay Protocols
Sample Preparation
100 mM stock solutions of compounds are prepared by dissolving the solid samples in 100% DMSO. The 10 mM stock solutions are prepared by 10-fold dilution of the 100 mM solutions with DMSO. Two-fold serial dilutions are performed in a V-shape 96-well plate.

The serial dilution solutions of samples are used as 50× solution in the assay. The final compound concentrations in the assay are in the range of 200 μM to 0.391 μM.

(2). Human Topoisomerase II DNA Decatenation Assay in the Absence of BSA

A negative control is the assay reaction with 20 mM EDTA. A positive control is the assay without any inhibitor. The background fluorescence of compounds is measured using the same compound concentrations with DNA and fluorescence dye.

The human topo II DNA decatenation assay kit, 96-Well Human Topo II DNA Decatenation Assay Kit Plus (from MoBiTec®, Catalog No. HDD96KE), is used for measurement of the inhibition.

The total volume of each reaction mixture is 50 μl. In a V-bottom assay plate, 1 μl of inhibitor and 24 μl of premix are mixed. The reaction is initiated with 25 μl of 20 mM $MgCl_2$. The premix is prepared by mixing 870 μl of $H_2O$, 300 μl of 10× assay buffer, 300 μl of 20 μg/ml concatenated DNA, 30 μl of 100 mM ATP and 1.5 μl of 10 U/μl human topoisomerase II alpha enzyme (topo II). The reaction mixture is incubated at room temperature for 60 min. Then 0.2 M EDTA (5 μl) is added to stop the reaction.

The final concentrations for the human topo II assay are 50 mM Tris-HCl, pH 8.0, 125 mM NaCl, 0.5 mM EDTA, 10 mM $MgCl_2$, 2 μg/ml concatenated DNA, 1 mM ATP and 5 U/ml human topo II alpha enzyme.

The sample (50 μl) is load onto a TDD filter plate on a vacuum manifold. Then a vacuum (80 kPa or 600 mmHg) is applied until the solution went through the filter. The filter is rinsed with 150 μl of the Rinse Buffer (10 mM Tris-HCl, pH 7.5, 10 mM NaCl). Finally the 1× fluorescence dye (50 μl) is added and the fluorescence intensity at 535 nm using the excitation wavelength at 485 nm is measured.

Results:

The results of the assay are presented in FIG. 1. Compounds: Adva-27afh=Example 1; Adva-27af=Example 2.

(3). Human Topoisomerase II DNA Decatenation Assay in the Presence of BSA

A negative control is the assay reaction with 20 mM EDTA. A positive control is the assay without any inhibitor. The background fluorescence of compounds is measured using the same compound concentrations with DNA and fluorescence dye.

The human topo II DNA decatenation assay kit, 96-Well Human Topo II DNA Decatenation Assay Kit Plus (from MoBiTec®, Catalog No. HDD96KE), is used for measurement of the inhibition.

The total volume of each reaction mixture is 50 μl. In a V-bottom assay plate, 1 μl of inhibitor and 24 μl of premix are mixed. The reaction is initiated with 25 μl of 20 mM $MgCl_2$. The premix is prepared by mixing 810 μl of $H_2O$, 300 μl of 10× assay buffer, 300 μl of 20 μg/ml concatenated DNA, 30 μl of 100 mM ATP and 30 μl of 500 U/ml human topoisomerase II alpha enzyme (topo II) in a enzyme dilution buffer containing 0.5 mg/ml BSA. The reaction mixture is incubated at room temperature for 40 min. Then 0.2 M EDTA (5 μl) is added to stop the reaction.

The final concentrations for the human topo II assay are 50 mM Tris-HCl, pH 8.0, 125 mM NaCl, 0.5 mM EDTA, 10 mM $MgCl_2$, 2 μg/ml concatenated DNA, 1 mM ATP, 5 U/ml human topo II alpha enzyme and 5 μg/ml BSA.

The sample (50 μl) is loaded onto a TDD filter plate on a vacuum manifold. Then a vacuum (80 kPa or 600 mmHg) is applied until the solution went through the filter. The filter is rinsed with 150 μl of the Rinse Buffer (10 mM Tris-HCl, pH 7.5, 10 mM NaCl). Finally the 1× fluorescence dye (50 μl) is added and the fluorescence intensity at 535 nm using the excitation wavelength at 485 nm is measured.

Figure 2:
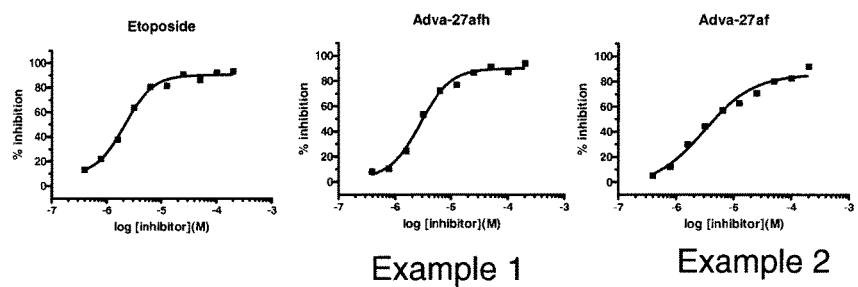
FIG. 2 illustrates the inhibition of human topoisomerase II DNA decatenation in the presence of BSA.
Figure 3A:
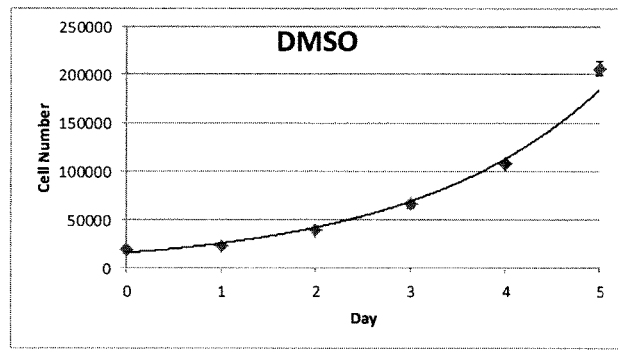
FIG. 3A illustrates the time-dependent growth of MCF-7/mdr cancer cells treated with 0.4% DMSO.
Figure 3B:
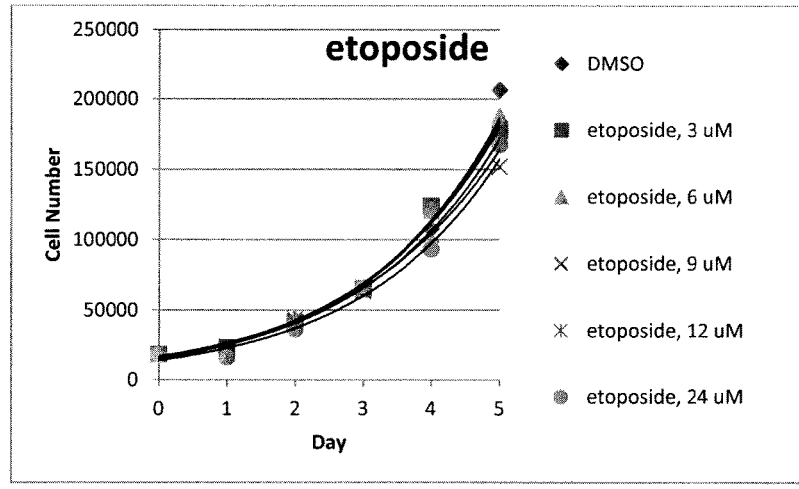
FIG. 3B illustrates the cell growth of MCF-7/mdr cancer cells upon treatment with etoposide.
Figure 3C:
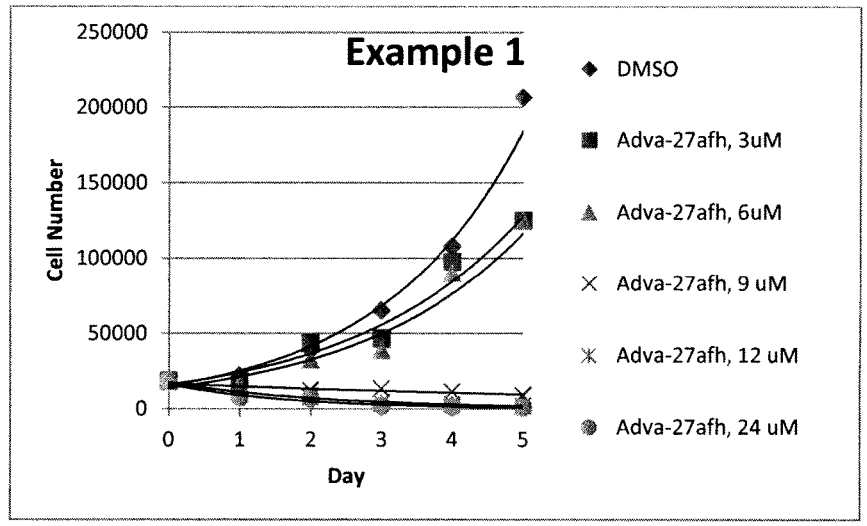
FIG. 3C illustrates the cell growth of MCF-7/mdr cancer cells upon treatment with the compound of Example 1.
Figure 3D:
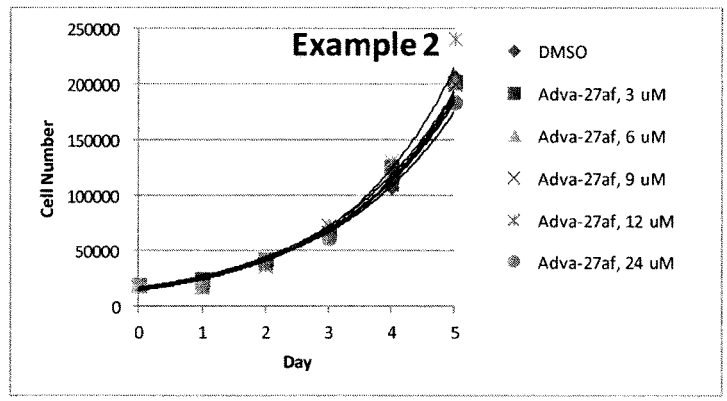
FIG. 3D illustrates the cell growth of MCF-7/mdr cancer cells upon treatment with the compound of Example 2.

Results:

The results of the assay are presented in FIG. 2. Compounds: Adva-27afh=Example 1; Adva-27af=Example 2.

3.2—In Vitro Evaluation of the Time Dependence of Growth Inhibitory Activity in a Human Breast Cancer Cell Line with Multidrug Resistance (MCF-7/Mdr)

(1). Cell Culture

Human breast carcinoma cell line with multiple-drug resistance (MCF-7/mdr) is provided from sponsor. MCF7/mdr cells are cultured in 37° C. $CO_2$ incubator in RPMI1640 media with 10% FBS, with addition of glutamine (2 mM), penicillin (100 I.U.) and streptomycin (100 μg/ml) and HEPES (10 mM) are added to the media. Cells are thawed and kept in 0.8 μM Doxorubicin (from Sigma-Aldrich® Canada, catalog number D1515) for a week prior to the study. During the course of study, there is no Doxorubicin in the culture media.

(2). Growth Inhibition Analysis.

MCF-7/mdr cells are plated at ~18000 cells/well in 12-well tissue culture plates on Day −1. Twenty-four (24) hours post-plating (DO), cells are treated with 0.4% DMSO, or test articles (Example 1, Example 2 and etoposide) at 3, 6, 9, 12, and 24 μM. The final concentration of DMSO is 0.4% for all wells treated with test articles.

At 0 (Day 0), 24 (Day 1), 48 (Day 2), 72 (Day 3), 96 (Day 4) and 120 (Day 5) hours post-treatment, one plate is retrieved and study terminated for time course analysis. Culture media are gently aspirated and cells washed once with 2 ml sterile PBS. Trypsin-0.25% EDTA (0.4 ml) is used to detach cells from the plate and 1 ml media is added to inactivate trypsin. Cells are transferred to 1.5 ml Eppendorf® tubes and spun at 2500 rpm for 2 minutes to collect cell pellets. Cell pellets are resuspended in 50 μl of PBS. Cells (20 μl) are mixed with 0.4% trypan blue staining solution (20 μl) for cell counting using a hemocytometer.

(3). Results:

The results showing the time-dependent growth of MCF-7/mdr cancer cells treated with the different compounds, or not are found in FIG. 3A-D. Compounds: Adva-27afh=Example 1. Adva-27af=Example 2.

3.3—In Vitro Evaluation of the Time Dependence of Growth Inhibitory Activity of in a Human Lung Carcinoma Cell Line with Multidrug Resistance (H69AR)

(1). Cell Culture

Human lung carcinoma cell line with multiple-drug resistance (H69AR) is purchased from American Tissue Culture Collection Via® Cedarlane® (Burlington, Ontario, Canada). H69AR cells are cultured in 37° C. $CO_2$ incubator in RPMI1640 media with 20% FBS, with addition of glutamine (2 mM), penicillin (100 I.U.) and streptomycin (100 μg/ml) and HEPES (10 mM) are added to the media. Cells are thawed and kept in increasing concentration of 0.1-0.5 μM Doxorubicin (from Sigma-Aldrich® Canada, catalog number D1515) for about one week prior to the study. During the course of study, there is no Doxorubicin in the culture media.

(2). Growth Inhibition Analysis.

H69AR cells are plated at ~50000 cells/well in 12-well tissue culture plates on Day −1. Twenty-four (24) hours post-plating (DO), cells are treated with 0.4% DMSO, or test articles (Example 1 and etoposide) at 3, 6, 9, 12, and 24 µM. The final concentration of DMSO is 0.4% for all wells treated with test articles.

At 0 (Day 0), 24 (Day 1), 48 (Day 2), 72 (Day 3), 96 (Day 4) and 120 (Day 5) hours post-treatment, one plate is retrieved and study terminated for time course analysis. Culture media are gently aspirated and cells washed once with 2 ml sterile PBS. Trypsin-0.25% EDTA (0.4 ml) is used to detach cells from the plate and 1 ml media is added to inactivate trypsin. Cells are transferred to 1.5 ml Eppendorf® tubes and spun at 2500 rpm for 2 minutes to collect cell pellets. Cell pellets are resuspended in 50 µl of PBS. Cells (20 µl) are mixed with 0.4% trypan blue staining solution (20 µl) for cell counting using a hemocytometer.

Figure 4A:
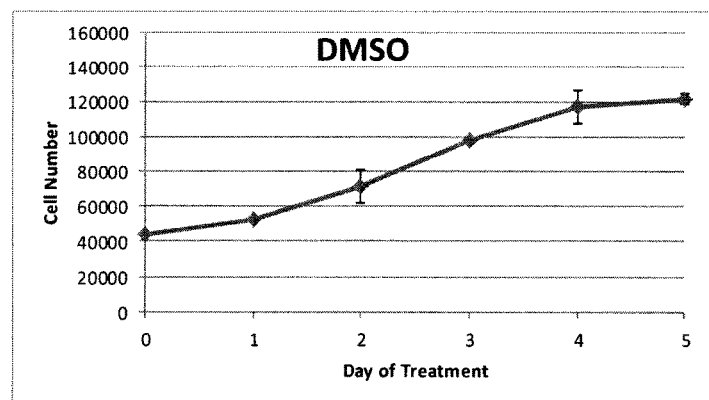
FIG. 4A illustrates time-dependent growth of H69AR cancer cells treated with 0.4% DMSO.
Figure 4B:
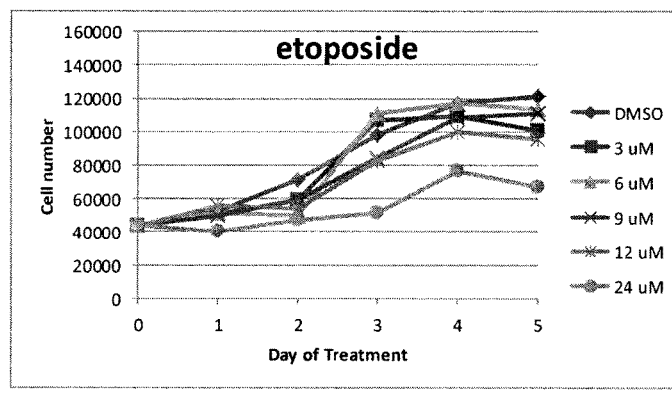
FIG. 4B illustrates cell growth of H69AR cancer cells upon treatment with etoposide.
Figure 4C:
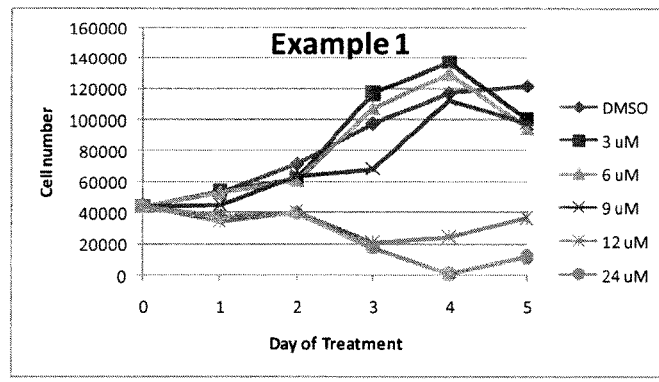
FIG. 4C illustrates cell growth of H69AR cancer cells upon treatment with the compound of Example 1.

(3). Results:

The results showing the time-dependent growth of H69AR cancer cells treated with the different compounds, or not are found in FIG. 4A-C. Compounds: Adva-27afh=Example 1.

3.4—In Vitro Evaluation of the Time Dependence of Growth Inhibitory Activity of in a Human Uterine Sarcoma Cancer Cell Line with Multidrug Resistance (MES-SA/DX5)

(1). Cell Culture

Human uterine sarcoma cell line with multiple-drug resistance (MES-SA/Dx5) is purchased from American Tissue Culture Collection® via Cedarlane® (Burlington, Ontario, Canada) (cat. CRL-1977). MES-SA/Dx5 cells are cultured in 37° C. $CO_2$ incubator in McCoy 5A media with 10% FBS, with addition of glutamine (2 mM), penicillin (100 I.U.) and streptomycin (100 µg/ml).

(2). Growth Inhibition Analysis.

MES-SA/Dx5 cells are plated at ~300000 cells/well in 12-well tissue culture plates on Day −1. Twenty-four (24) hours post-plating (DO), cells are treated with 0.4% DMSO, or test articles (Example 1 and etoposide) at 3, 6, 9, 12, and 24 µM. The final concentration of DMSO is 0.4% for all wells treated with test articles.

At 0 (Day 0), 24 (Day 1), 48 (Day 2), 72 (Day 3), 96 (Day 4) and 120 (Day 5) hours post-treatment, one plate is retrieved and study terminated for time course analysis. Culture media are gently aspirated and cells washed once with 2 ml sterile PBS. Trypsin-0.25% EDTA (0.4 ml) is used to detach cells from the plate and 1 ml media is added to inactivate trypsin. Cells are transferred to 1.5 ml Eppendorf® tubes and spun at 2500 rpm for 2 minutes to collect cell pellets. Cell pellets are resuspended in 50 µl of PBS. Cells (20 µl) are mixed with 0.4% trypan blue staining solution (20 µl) for cell counting using a hemocytometer.

Figure 5A:
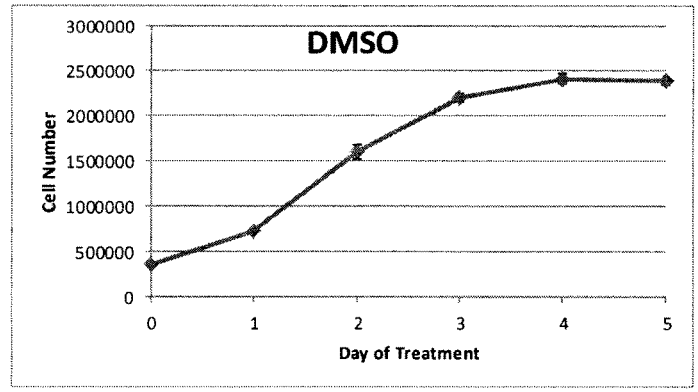
FIG. 5A illustrates time-dependent growth of MES-SA/Dx5 cancer cells treated with 0.4% DMSO.
Figure 5B:
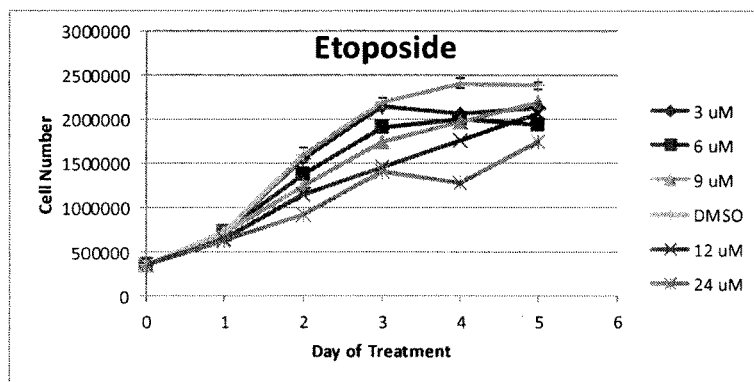
FIG. 5B illustrates cell growth of MES-SA/Dx5 cancer cells upon treatment with etoposide.
Figure 5C:
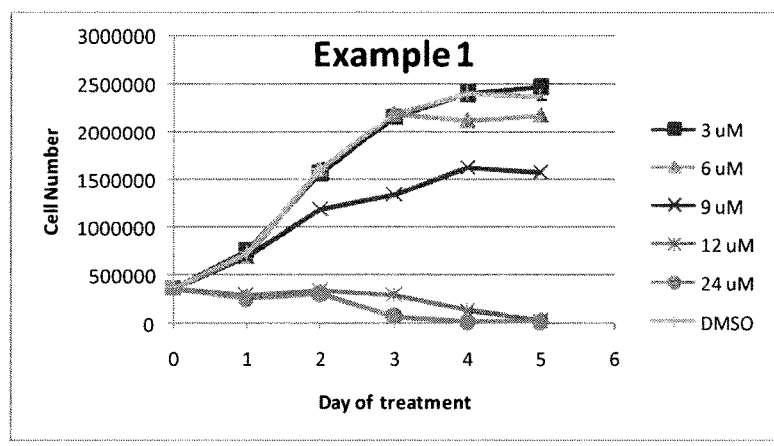
FIG. 5C illustrates cell growth of MES-SA/Dx5 cancer cells upon treatment with the compound of Example 1.

(3). Results:

The results showing the time-dependent growth of MES-SA/Dx5 cancer cells treated with the different compounds, or not are found in FIG. 5A-C. Compounds: Adva-27afh=Example 1.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method for preparing a compound of Formula I:

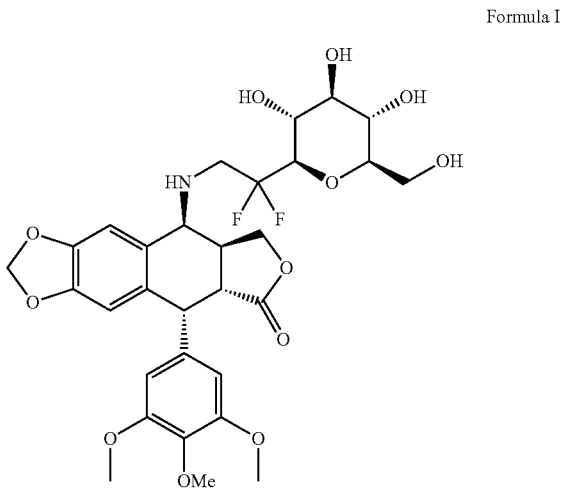 [SMILES: COc1cc([C@@H]2c3cc4c(cc3[C@@H](NCC(F)(F)[C@@H]3O[C@H](CO)[C@@H](O)[C@H](O)[C@H]3O)[C@H]3COC(=O)[C@H]23)OCO4)cc(OC)c1OC]

Formula I or a pharmaceutically acceptable salt, hydrate or solvate thereof, comprising the steps of:

1) obtaining a compound of formula IV by epimerization and then substitution of an alcohol function in position 4 of podophyllotoxin or demethylated podophyllotoxin by an azido group subsequently reduced into an amine group

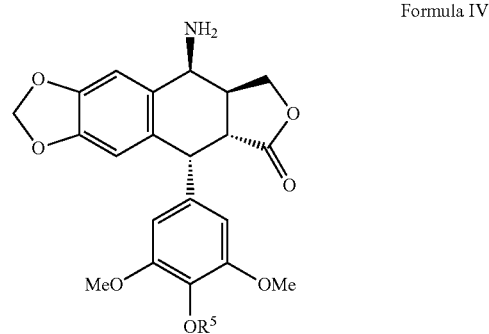

Formula IV wherein $R^5$ is a methyl group;

2) obtaining a compound of Formula V

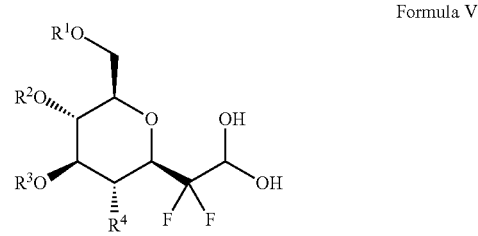

Formula V wherein $R^1$, $R^2$, $R^3$ are a hydrogen atom or a protective group for a hydroxyl, wherein $R^4$ is a hydroxyl group or a protective group for a hydroxyl group, via the following reaction sequence:

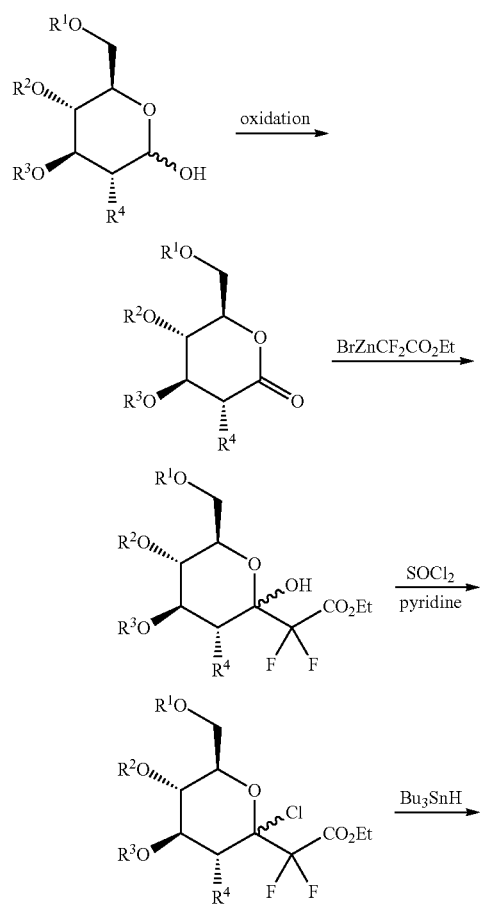
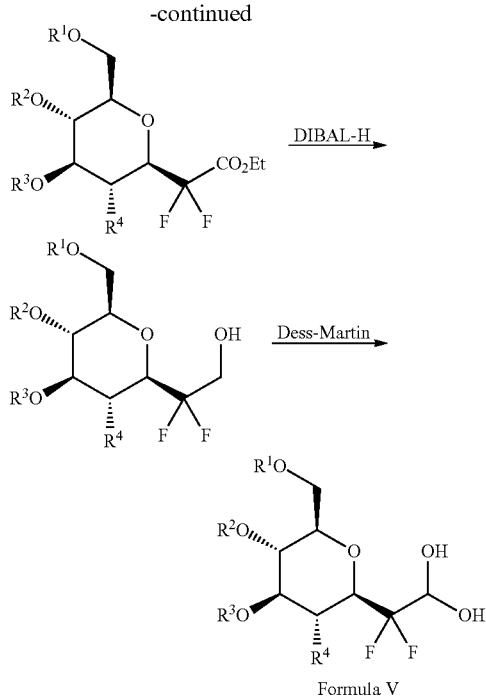
wherein $R^1$, $R^2$, $R^3$, $R^4$ are as defined in Formula V; and
3) coupling said compound of Formula IV with said compound of formula V.
2. The method of claim 1, wherein the protective group for a hydroxyl group is selected from the group consisting of a linear alkyl group, a branched alkyl group, a benzyl group, a benzoyl group, an acetyl group and a pivaloyl group.
* * * * *

UNITED STATES PATENT AND TRADEMARK OFFICE
CERTIFICATE OF CORRECTION

PATENT NO. : 10,272,065 B2  
APPLICATION NO. : 14/760021  
DATED : April 30, 2019  
INVENTOR(S) : Steve N. Slilaty Page 1 of 1

It is certified that error appears in the above-identified patent and that said Letters Patent is hereby corrected as shown below:

On the Title Page

Item (73), should read:  
Assignees: SUNSHINE BIOPHARMA INC.  
        6500 Trans-Canada Highway  
        4th Floor  
        Pointe-Claire, QC H9R 0A2  
        Canada Signed and Sealed this  
Twentieth Day of October, 2020

Andrei Iancu  
*Director of the United States Patent and Trademark Office*